(12) United States Patent
Cui et al.

(10) Patent No.: US 11,752,316 B2
(45) Date of Patent: Sep. 12, 2023

(54) INTRA-CAVITY CIRCULATION HEAT PERFUSION APPARATUS

(71) Applicant: GUANGZHOU BRIGHT MEDICAL TECHNOLOGY CO., LTD., Guangzhou (CN)

(72) Inventors: Shuzhong Cui, Guangzhou (CN); Diwen Huang, Guangzhou (CN); Hongsheng Tang, Guangzhou (CN); Bin Wang, Guangzhou (CN); Qiang Ruan, Guangzhou (CN); Jing Li, Guangzhou (CN)

(73) Assignee: GUANGZHOU BRIGHT MEDICAL TECHNOLOGY CO., LTD., Guangzhou (CN)

( * ) Notice: Subject to any disclaimer, the term of this patent is extended or adjusted under 35 U.S.C. 154(b) by 624 days.

(21) Appl. No.: 16/954,029

(22) PCT Filed: Jul. 27, 2018

(86) PCT No.: PCT/CN2018/097600
§ 371 (c)(1),
(2) Date: Jun. 15, 2020

(87) PCT Pub. No.: WO2019/205327
PCT Pub. Date: Oct. 31, 2019

(65) Prior Publication Data
US 2021/0162188 A1   Jun. 3, 2021

(30) Foreign Application Priority Data
Apr. 28, 2018   (CN) .......................... 201810403513.5

(51) Int. Cl.
*A61M 31/00*   (2006.01)
*A61F 7/12*   (2006.01)

(52) U.S. Cl.
CPC ................ *A61M 31/00* (2013.01); *A61F 7/12* (2013.01); *A61M 2205/3337* (2013.01);
(Continued)

(58) Field of Classification Search
CPC .......... A61M 31/00; A61M 2205/3337; A61M 2205/505; A61M 2210/1085;
(Continued)

(56) References Cited

U.S. PATENT DOCUMENTS 6,610,024 B1   8/2003   Benatti
2008/0234619 A1   9/2008   Fausset et al.
(Continued)

FOREIGN PATENT DOCUMENTS

CN   1562400   1/2005
CN   101686872   3/2010
(Continued)

OTHER PUBLICATIONS

Ba Mingchen et al, "Bladder intracavitary hyperthermic perfusion chemotherapy for the prevention of recurrence of non-muscle invasive bladder cancer after transurethral resection," Oncology Reports, vol. 37, No. 5, May 11, 2017, pp. 2761-2770.
(Continued)

*Primary Examiner* — James D Ponton
*Assistant Examiner* — Neeraja Gollamudi
(74) *Attorney, Agent, or Firm* — Seyfarth Shaw LLP

(57) ABSTRACT

An intra-cavity circulation heat perfusion apparatus, comprising a casing, an electromagnetic induction heating means, and a controller. The electromagnetic induction heating means comprises a tray and an electromagnetic induction coil; the tray is used for bearing a heating tank; a master control unit of the controller controls the electromagnetic induction coil to be electrified to heat the heating tank, so as to indirectly heat a medicinal liquid in a liquid
(Continued)

storage chamber; a data acquisition unit is used for acquiring medicinal liquid temperature values of the heating tank, a liquid outlet pipeline, and a liquid return pipeline and transferring same to the master control unit; the master control unit controls a power control unit according to the medicinal liquid temperature values to control a heating power of the electromagnetic induction coil.

20 Claims, 22 Drawing Sheets

(52) U.S. Cl.
CPC . *A61M 2205/368* (2013.01); *A61M 2205/505* (2013.01); *A61M 2210/1085* (2013.01)

(58) Field of Classification Search
CPC . A61M 2205/36; A61F 7/12; A61F 2007/126; A61H 2009/0042; A61H 2201/0242
See application file for complete search history.

(56) References Cited

U.S. PATENT DOCUMENTS

2015/0223892 A1* 8/2015 Miller .................. A61B 50/18
345/174

2017/0165409 A1* 6/2017 Li ........................ A61M 1/77
2017/0202704 A9 7/2017 Landy et al.

FOREIGN PATENT DOCUMENTS

| CN | 202313910 | 7/2012 |
| CN | 202892196 U | 4/2013 |
| CN | 203954449 U | 11/2014 |
| CN | 104667361 | 6/2015 |
| CN | 205084071 U | 3/2016 |
| CN | 105498003 A | 4/2016 |
| CN | 105727426 A | 7/2016 |
| CN | 107157648 A | 9/2017 |
| CN | 108175894 A | 6/2018 |
| EP | 19672222 A2 | 8/2008 |

OTHER PUBLICATIONS

Australian Examination Report No. 1 for corresponding Application No. 2018421234 dated Jun. 1, 2021, 4 pages.
Supplemental European Search Report for corresponding Application No. 18916527.7 dated May 11, 2021, 12 pages.
International Search Report for Application No. PCT/CN2018/097600, dated Jan. 23, 2019, 2 pages.
Written Opinion for Application No. PCT/CN2018/097600, dated Jan. 23, 2019, 4 pages.

* cited by examiner

# US 11,752,316 B2

INTRA-CAVITY CIRCULATION HEAT PERFUSION APPARATUS

CROSS REFERENCE TO RELATED APPLICATIONS

This is a U.S. National Stage application of, and claims priority to, PCT/CN2018/097600, filed Jul. 27, 2018, which further claims priority to Chinese Patent Application No. 201810403513.5, filed Apr. 28, 2018, the disclosures of which are incorporated herein by reference in their entirety.

TECHNICAL FIELD

The present disclosure relates to the technical field of medical instruments, and more particularly, to a device of intracavitary circulatory hyperthermic perfusion.

BACKGROUND

Bladder cancer is the most common tumor of the urinary system. In China, the new patient with bladder cancer is about 6 ten thousand per year, the incidence of the bladder cancer ranks seventh among that of male malignancies. The bladder cancer is classified into: a non-muscle invasive bladder cancer and a muscle invasive bladder cancer, and the non-muscle invasive bladder cancer is characterized by high recurrence and low progression. The treatment of the non-muscle invasive bladder cancer is usually a surgical treatment, and a transurethral resection of bladder tumor (TURBT) is mainly used. The non-muscle invasive bladder cancer has a high postoperative recurrence rate, and 20% to 70% of patients relapse within one year after TURBT. A perfusion treatment after TURBT is a very important means for preventing recurrence.

The perfusion treatment device can be applied to the bladder for treatment, and can also be applied to the chest cavity, the abdominal cavity, the pelvis cavity, the rectum and the like for treatment. When a conventional perfusion treatment device is used for treating the bladder, a perfusion treatment device is used for a normal temperature perfusion after a resection operation of the bladder tumor. 50 mg of pirarubicin is dissolved in 50 ml of normal saline to prepare a medicinal solution, and then the medicinal solution is extracted with a syringe and is injected into the bladder of a patient through a urinary catheter. The medicinal solution is discharged after staying in the bladder of the patient for 45 min to 60 min. However, the conventional perfusion treatment device has a poor treatment effect.

SUMMARY

Based on this, in view of the aforementioned technical problems, it is necessary to provide a device of intracavitary circulatory hyperthermic perfusion that can effectively improve the treatment effect.

A device of intracavitary circulatory hyperthermic perfusion includes:
 a housing;
 an electromagnetic induction heating device disposed on the housing, the electromagnetic induction heating device including a tray and an electromagnetic induction coil, the electromagnetic induction coil being disposed on one side of the tray and configured to heat a heating tank capable of being carried on the tray;
 a controller including a main control unit, a data acquisition unit, and a power control unit, wherein the data acquisition unit and the power control unit are electrically coupled to the main control unit, the data acquisition unit is configured to acquire temperature values of a medicinal solution in the heating tank, a liquid outlet pipeline, and a liquid return pipeline and to transmit the temperature values to the main control unit, and the main control unit controls the power control unit according to the temperature values of the medicinal solution to control a heating power of the electromagnetic induction coil.

The aforementioned device of intracavitary circulatory hyperthermic perfusion has at least the following advantages.

The tray is configured to carry the heating tank. During operation, the main control unit of the controller controls the electromagnetic induction coil to be energized to heat the heating tank, thereby indirectly heating the medicinal solution in the liquid storage cavity to raise the temperature of the medicinal solution. The data acquisition unit is configured to acquire the temperature values of the medicinal solution in the heating tank, the liquid outlet pipeline, and the liquid return pipeline and to transmit the temperature values to the main control unit, and the main control unit controls the power control unit according to the temperature values of the medicinal solution to control the heating power of the electromagnetic induction coil. When the temperature of the medicinal solution reaches a predetermined temperature, the temperature is kept constant. The medicinal solution is heated to the predetermined temperature before being introduced into the bladder for treatment, thus, after the liquid medicine is introduced into the bladder, a thermal killing mechanism can be fully exerted, metastatic cancer cells that are widely planted on serosa are killed, the lesions that cause the malignant effusion can be eliminated, so that the purpose of effectively treating the cancerous effusion is achieved, and the treatment effect is effectively improved.

DETAILED DESCRIPTION OF EMBODIMENTS

In order to make the foregoing objects, features, and advantages of the present disclosure more apparent and intelligible, specific embodiments of the present disclosure are described in detail below with reference to the accompanying drawings. Numerous specific details are set forth in the following description in order to fully understand the present disclosure. However, the present disclosure can be implemented in many other ways than those described herein, and those skilled in the art can make similar improvements without departing from the content of the present disclosure, so the present disclosure is not limited by the specific implementations disclosed below.

It should be noted that when an element is referred to as being "fixed to" another element, it may be directly on the other element or there may be an intermediate element. When an element is considered to be "connected" to another element, it can be directly connected to another element or connected to another element with an intermediate element. The terms "vertical", "horizontal", "left", "right" and similar expressions used herein are for illustrative purposes only and are not meant to be the only implementations.

Unless defined otherwise, all technical and scientific terms used herein have the same meaning as commonly understood by those skilled in the art to which the present disclosure belongs. The terms used in the description of the present disclosure are only for the purpose of describing specific embodiments, and are not intended to limit the present disclosure. The technical features of the embodiments described above can be arbitrarily combined. In order to simplify the description, all possible combinations of the technical features in the above embodiments have not been described. However, as long as there is no contradiction in the combinations of these technical features, all combinations should be considered within the scope of the present description.

Figure 1:
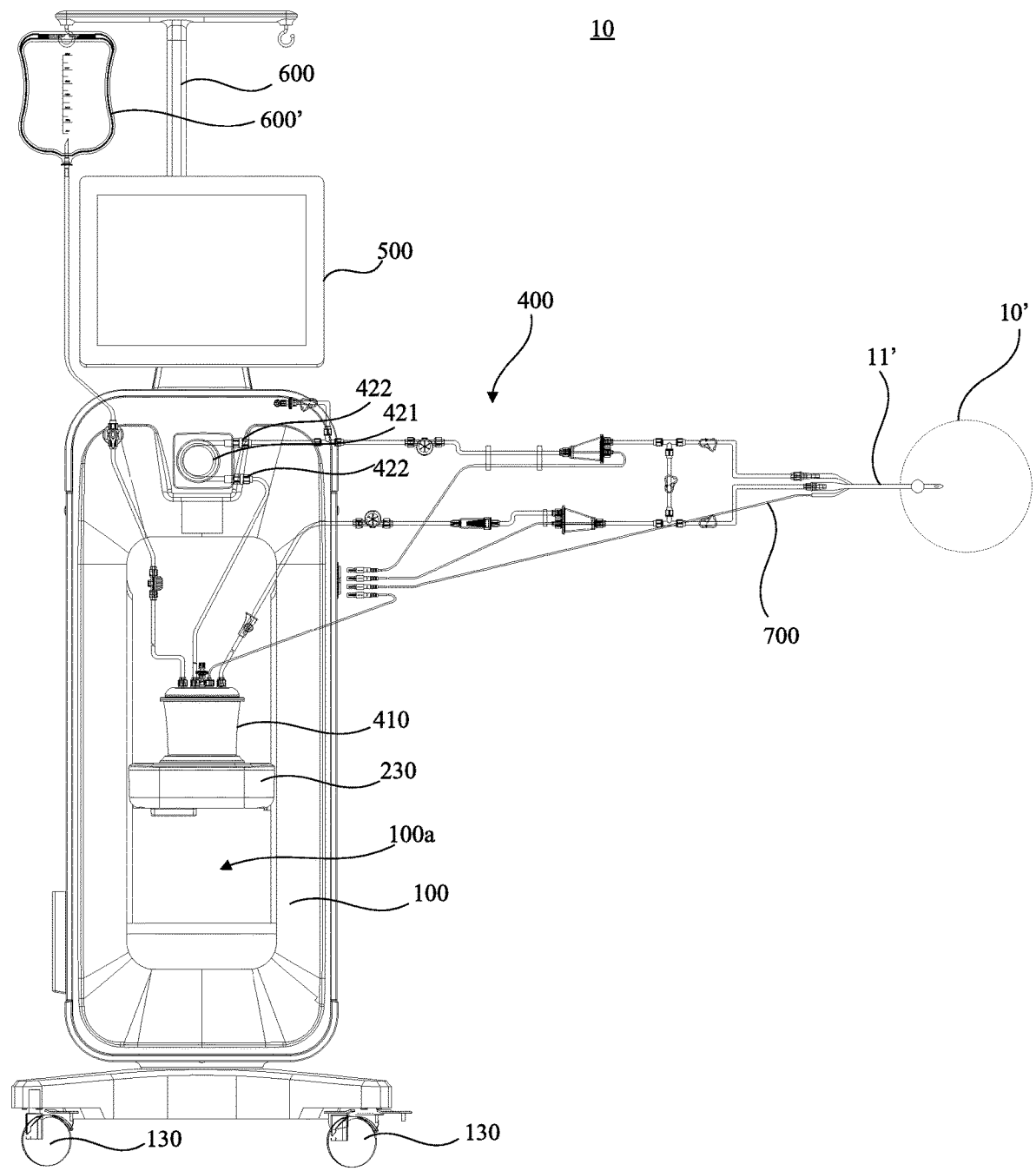
FIG. 1 is a schematic view of a device of intracavitary circulatory hyperthermic perfusion in accordance with an embodiment.

Referring to FIG. 1, a device of intracavitary circulatory hyperthermic perfusion 10 in accordance with an embodiment is mainly used to perfuse chemotherapeutic drugs heated to a certain temperature into a body cavity, which can fully exert a thermal killing mechanism to kill metastatic cancer cells that are widely planted on serosa and to eliminate the lesions causing the malignant effusion, so that the purpose of effectively treating cancerous effusion is achieved, and the treatment effect is effectively improved. The device of intracavitary circulatory hyperthermic perfusion 10 can be applied to various body cavities such as the bladder, the chest cavity, the abdominal cavity, the pelvic cavity, or the rectum and the like, thereby achieving the purpose of improving the treatment effect. The present embodiment is mainly described in detail by taking the example of the application to the bladder 10', but this does not limit the scope of the application of the device of intracavitary circulatory hyperthermic perfusion 10.

Figure 2:
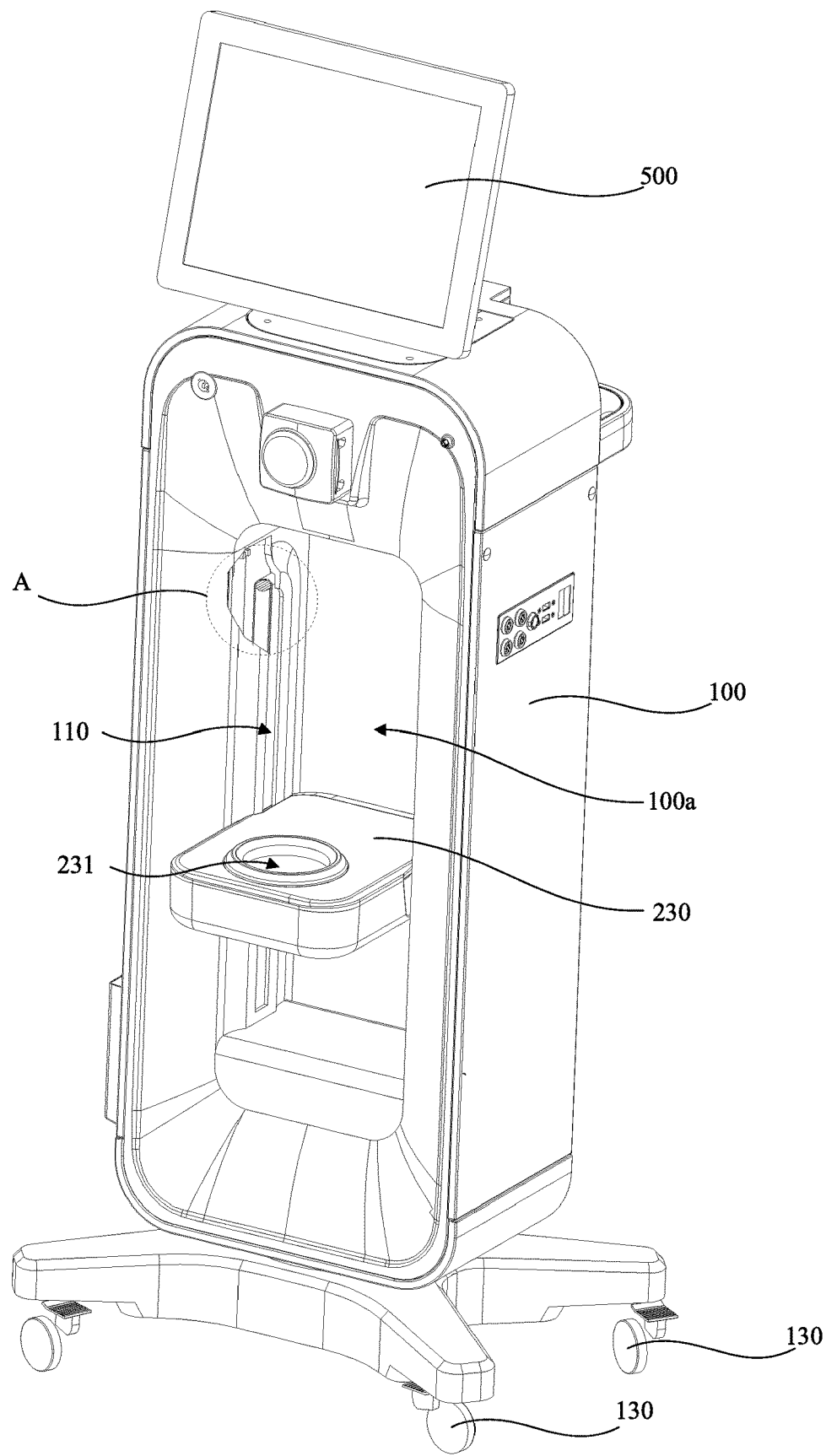
FIG. 2 is a partial schematic view of FIG. 1.
Figure 4:
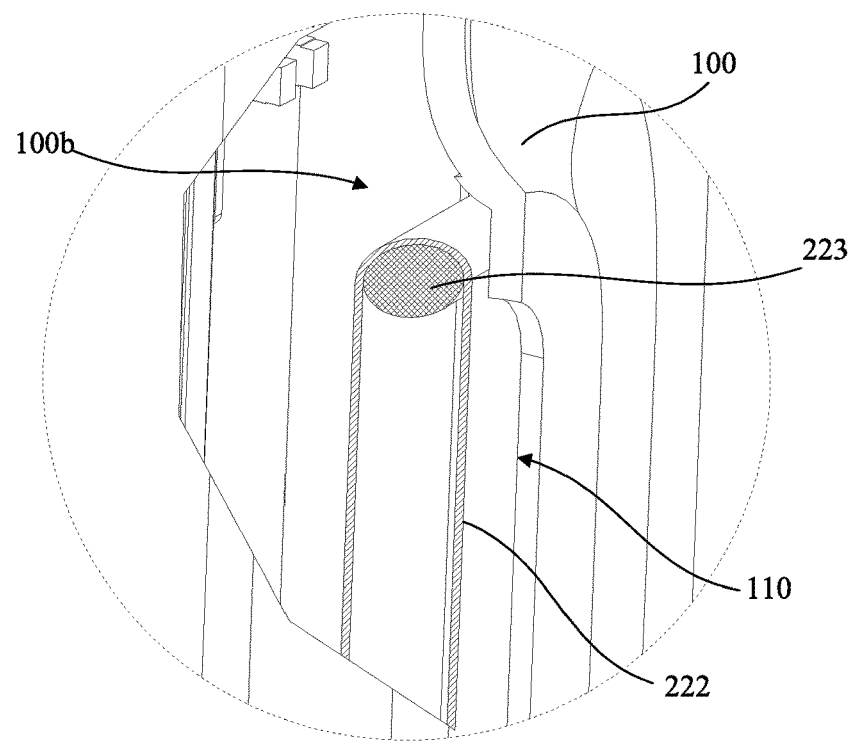
FIG. 4 is a partially enlarged view of an A-portion shown in FIG. 2.

Referring to FIG. 2 and FIG. 4 together, specifically, the device of intracavitary circulatory hyperthermic perfusion 10 includes a housing 100, a lifting mechanism 200, a dustproof assembly 220, an electromagnetic induction heating device (not shown), a circulation pipeline for hyperthermic perfusion 400, a controller (not shown), a touch display 500, and an infusion rod 600. The housing 100 is mainly used to carry and support.

An accommodating cavity 100a is formed in the middle of the housing 100 and penetrates through two opposite sides of the housing 100, so that a user can directly observe components and parts in the accommodating cavity 100a and can directly manipulate the components and parts located in the accommodating cavity 100a by hand. An interior of the housing 100 is hollow. Therefore, a storage cavity 100b is formed in the interior of the housing 100. A sliding groove 110 is formed on a side wall of the housing 100 and is in communication with the accommodating cavity 100a.

The touch display 500 is disposed on the housing 100 and is electrically coupled to the controller. Specifically, the touch display 500 is disposed on a top of the housing 100, a human-computer interactive operation of the device of intracavitary circulatory hyperthermic perfusion 10 can be achieved by touching the touch display 500, thereby improving convenience. The bottom of the housing 100 is further provided with a rotating wheel 130 to improve convenience of transportation and save time and labor. The housing 100 is further provided with an infusion rod 600, which is used for hanging a medicine solution bag 600' or a medicine solution bottle.

Figure 3:
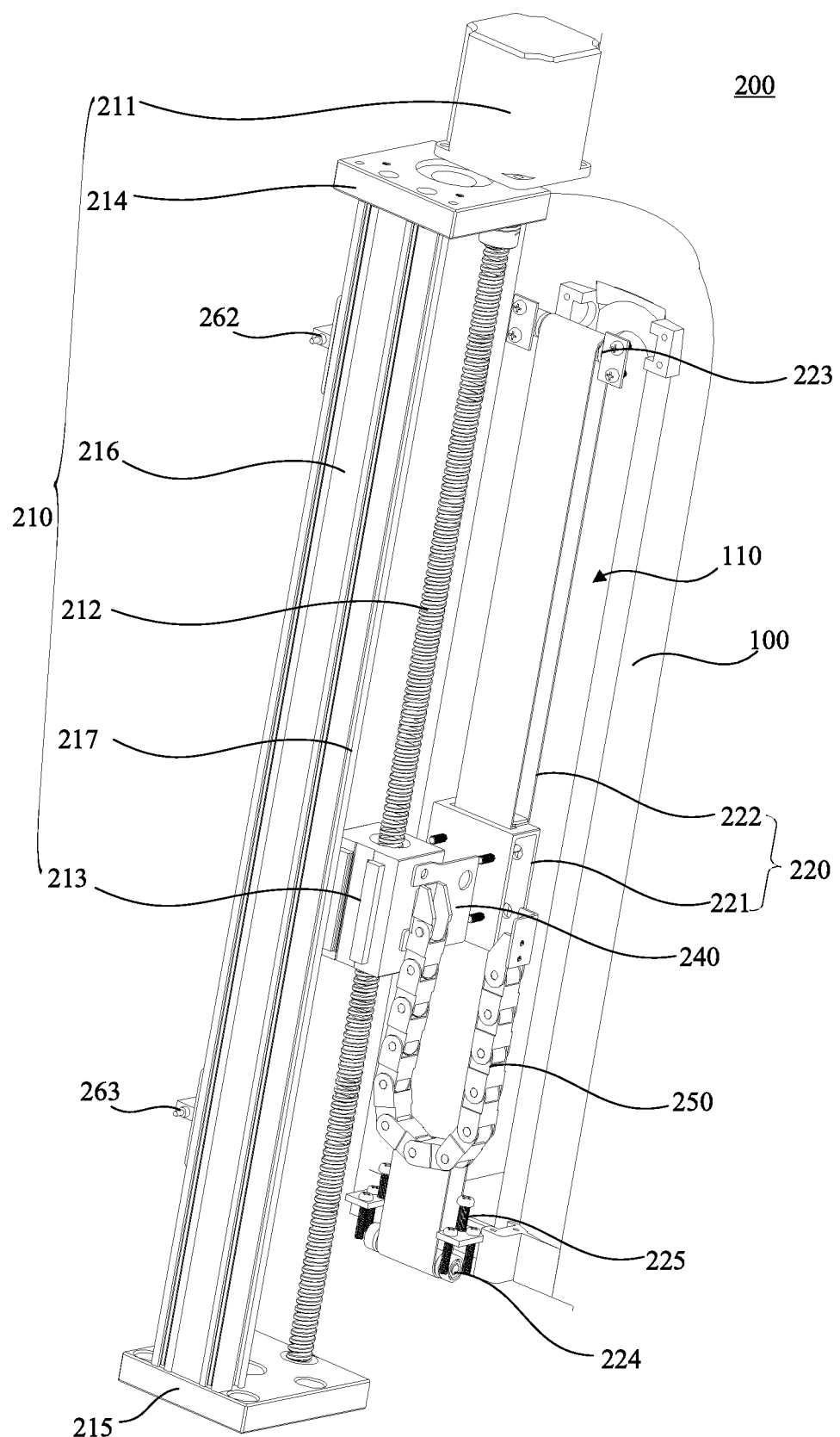
FIG. 3 is a partial schematic view of FIG. 2.
Figure 5:
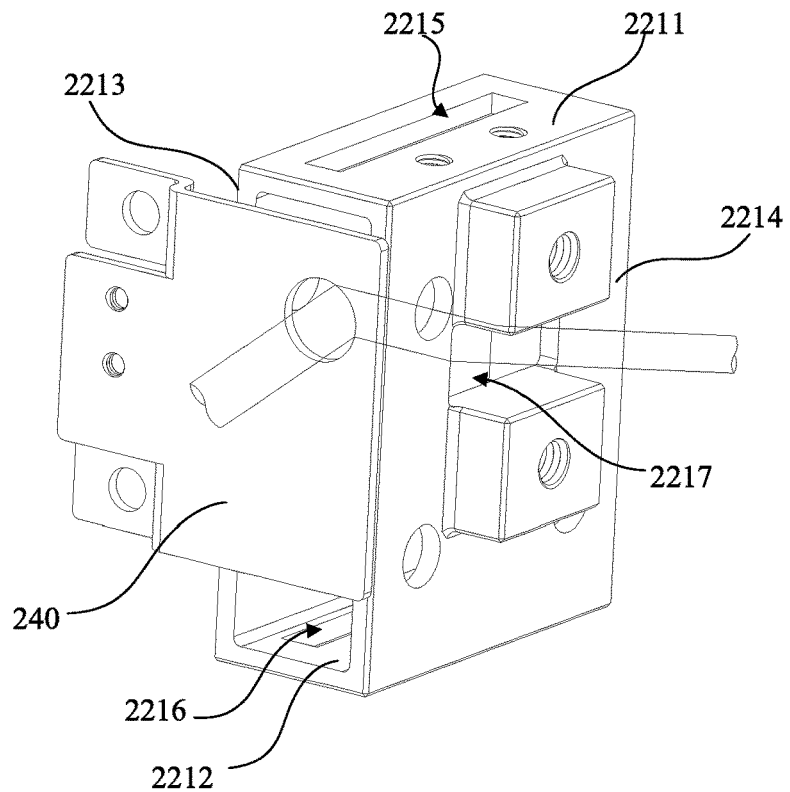
FIG. 5 is a partial schematic view of FIG. 3.

Referring to FIG. 3 and FIG. 5 together, the lifting mechanism 200 includes a lifting assembly 210 and a lifting platform 230. The lifting assembly 210 is disposed inside the housing 100. The lifting assembly 210 includes a first driving source 211, a driving shaft 212, and a lifting block 213. The first driving source 211 is capable of driving the lifting block 213 to move reciprocally along a lifting direction through the driving shaft 212.

Specifically, in the present embodiment, the first driving source 211 is a motor, and the motor may be a stepping motor. The driving shaft 212 is a lead screw, and the lifting block 213 is rotatably disposed on the lead screw. The motor can drive the lead screw to rotate, and the lifting block 213 can rotate relative to the lead screw to realize the reciprocating movement along the lifting direction.

The lifting assembly 210 further includes a motor fixing base 214, which is fixed inside the housing 100, and the motor is mounted on the motor fixing base 214. Since the driving shaft 212 is the lead screw, the lifting assembly 210 further includes a lead screw base 215 that is fixed inside the housing 100. One end of the lead screw is connected to the motor through a coupler, and the other end of the lead screw is disposed on the lead screw base 215.

Specifically, in the present embodiment, since the lead screw cannot be directly stressed, the lifting assembly 210 further includes a support frame 216 and a sliding rail 217. The support frame 216 is fixed inside the housing 100, and the sliding rail 217 is fixed on the support frame 216. The lifting block 213 is slidably disposed on the sliding rail 217. For example, both ends of the support frame 216 are respectively fixed on the motor fixing base 214 and the lead screw base 215, and the support frame 216 is fixed on the housing 100 through the motor fixing base 214 and the lead screw base 215. Therefore, the support frame 216 can be used to support the lead screw, thereby preventing the lead screw from being directly stressed.

Certainly, in other embodiments, the first driving source 211 may also be a cylinder. Correspondingly, the driving shaft 212 is a piston rod, and the lifting block 213 is fixed on the piston rod. The cylinder can drive the piston rod to move reciprocally along the lifting direction, so as to drive the lifting block 213 to move reciprocally along the lifting direction. Certainly, in another embodiment, the first driving source 211 may also be a motor, and the driving shaft 212 is a linear guide rail. The motor can drive the lifting block 213 to move up and down along the linear guide rail.

The dustproof assembly 220 includes a lifting seat 221, a dustproof belt 222, an upper rolling shaft 223, and a lower rolling shaft 224. The lifting seat 221 is fixed on the lifting block 213 and moves along with the movement of the lifting block 213. Both the upper rolling shaft 223 and the lower rolling shaft 224 are rotatably disposed inside the housing 100. For example, the upper rolling shaft 223 and the lower rolling shaft 224 may be rotatably mounted inside the housing 100 by a fastener. One end of the dustproof belt 222 is fixed on the lifting seat 221, and the other end of the dustproof belt 222 is fixed on the lifting seat 221 after passing around the upper rolling shaft 223, passing through the lifting seat 221, and passing around the lower rolling shaft 224.

The dustproof belt 222 can be made of cloth material or made of a leather belt material. Therefore, compared with the conventional foldable dustproof structure, the dustproof belt 222 adopted in the present embodiment does not shrink, and therefore, the dustproof belt 222 does not cause the phenomenon that the dustproof structure breaks up or cannot closely adhere to the sliding groove 110 or hinders the movement of the lifting block 213 during a shrinking process. In addition, compared with the foldable organ-type enclosure cloth, the dustproof assembly 220 in the present embodiment has a smaller volume, and meets the requirements for miniaturization. The lifting seat 221 has a mounting portion exposed to the casing 100 through the sliding slot 110 of the casing 100, and the dust-proof belt 222 is attached to the inner side wall of the casing 100 to shield the sliding slot 110. The lifting seat 221 is provided with a mounting portion exposed to the housing 100 through the sliding groove 110 on the housing 100, and the dustproof belt 222 abuts against an inner side wall of the housing 100 to shield the sliding groove 110.

The lifting seat 221 includes a top plate 2211, a bottom plate 2212, a first side plate 2213 and a second side plate 2214 which are oppositely disposed. The first side plate 2213 and the second side plate 2214 are located between the top plate 2211 and the bottom plate 2212. The top plate 2211 is provided with a first through hole 2215, and the bottom plate 2212 is provided with a second through hole 2216. After passing around the upper rolling shaft 223, the dustproof belt 222 sequentially passes through the first through hole 2215 and the second through hole 2216, and then passes around the lower rolling shaft 224. The first side plate 2213 is fixed on the lifting block 213, the second side plate 2214 faces the sliding groove 110, and the mounting portion is located on the second side plate 2214. Therefore, one side of the dustproof belt 222 is fixed on the lifting seat 221, and the other side of the dustproof belt 222 passes through the lifting seat 221, that is, the dustproof belt 222 is limited by the lifting seat 221 to prevent from being recessed under a slight external force. For example, the dustproof belt 222 may be fixed on the lifting seat 221 by a fastener.

Certainly, in other embodiments, the lifting seat 221 may also be a square hollow structure. The lifting seat 221 is provided with the first through hole 2215 at a top thereof and the second through hole 2216 at a bottom thereof. After passing around the upper rolling shaft 223, the dustproof belt 222 sequentially passes through the first through hole 2215 and the second through hole 2216, and then passes around the lower rolling shaft 224. One side of the lifting seat 221 is fixed on the lifting block 213, and the opposite side of the lifting seat 221 faces the sliding groove 110. The mounting portion is located on the opposite side of the lifting seat 221.

The lifting platform 230 is fixed on the mounting portion and is located outside the housing 100. The lifting platform 230 moves along with the movement of the lifting seat 221. A guide rail can also be formed on the other side wall of the housing 100 opposite to the sliding groove 110, and the other side of the lifting platform 230 matches with the guide rail. The guide rail has a certain guiding effect on the lifting platform 230 to prevent the lifting platform 230 from shaking during the lifting process.

The lifting mechanism 200 further includes a mounting block 240, which is disposed on the lifting seat 221. The second side plate 2214 is provided with a via hole 2217. A tank chain 250 is mounted on the mounting block 240. One end of the tank chain 250 is fixed on the housing 100 and the other end of the tank chain 250 is fixed on the mounting block 240. Moreover, the structure of the lifting seat 221 and the mounting block 240 is utilized, so that the wire passing requirement of the cable is met, and the influence on the movement of parts is avoided. Therefore, one end of the tank chain 250 is lifted along with the lifting of the lifting block 213. A circuit board of the lifting platform 230 is led out by a cable, and one end of the cable passes through the via hole 2217 and turns into the tank chain 250. The addition of the tank chain 250 can ensure that the bending radius of the cable is not too small, which reduces the fatigue strength and prolongs the service life. In addition, the structure of the lifting seat 221 and the mounting block 240 is utilized, so that the wire passing requirement of the cable is realized without affecting the movement of components.

The dustproof assembly also includes a travel switch trigger piece, an upper photoelectric switch 262, and a lower photoelectric switch 263. The travel switch trigger piece is disposed on the lifting block 213, the upper photoelectric switch 262 is disposed on the support frame 216, and the lower photoelectric switch 263 is disposed on the support frame 216 and is located below the upper photoelectric switch 262. The upper photoelectric switch 262 is used for the upper positioning, and the lower photoelectric switch 263 is used for the lower positioning.

When the lifting block 213 performs the lifting movement, the travel switch trigger piece may shield the upper photoelectric switch 262 or the lower photoelectric switch 263. At this time, a position feedback signal will be generated, so that the controller can send a command of stopping or reversing to the motor.

The dustproof assembly 220 further includes a tightness-adjusting member 225, which is configured to adjust the tightness of the dustproof belt 222. The tightness of the dustproof belt 222 can be adjusted by the tightness-adjusting member 225, so that the dustproof belt 222 can be tightened or loosened. Therefore, it is achieved that in the lifting process of the lifting platform 230, the sliding groove 110 is in a state of being completely shielded by the dustproof belt 222. Specifically, the tightness-adjusting member 225 may be a tightness-adjusting nut, and the tightness of the dustproof belt 222 can be adjusted by screwing the tightness-adjusting nut.

Before starting treatment, an operator is generally in a standing state, and the heating tank is expected to be higher at this moment to prevent the operator from bending or squatting; during treatment, a patient is generally lying down, at this time, the height of the heating tank is expected to be less than the height of a sickbed, so that the treatment liquid in the bladder can be guided through the connecting pipeline to flow back into the heating tank more smoothly under the action of gravity and siphon. Therefore, the driving shaft 212 can be driven by the first driving source 211 to operate, thereby allowing the lifting block 213 to move up or down along the lifting direction, which drives the lifting platform 230 to move up or down, so that the heating tank carried on the lifting platform 230 can perform the lifting movement. Since the lifting platform 230 is fixed on the mounting portion of the mounting base 240, the mounting portion is exposed to the housing 100 through the sliding groove 110 on the housing 100, and since the other end of the dustproof belt 222 is fixed on the lifting seat 221 after passing around the upper rolling shaft 223, passing through the lifting seat 221, and passing around the lower rolling shaft 224, the dustproof belt 222 can always abut against the inner side wall of the housing 100. Therefore, the dustproof belt 222 can always cover the sliding groove 110 in the lifting process, which effectively prevents sundries or dust from entering the interior of the housing 100. Certainly, in other embodiments, the lifting mechanism and the dustproof assembly can be omitted, and the heating tank can be directly fixed on the housing.

Referring to FIG. 1 and FIG. 2 again, the electromagnetic induction heating device is disposed on the housing 100. Specifically, the electromagnetic induction heating device is indirectly disposed on the housing 100 through the lifting platform 230. For example, the lifting platform 230 is hollow and is provided with a positioning hole 231. The electromagnetic induction heating device is located in the lifting platform 230. Certainly, in other embodiments, when the lifting mechanism and the dustproof assembly are omitted, the electromagnetic induction heating device may also be directly disposed on the housing 100.

The electromagnetic induction heating device includes a tray and an electromagnetic induction coil, which is disposed on one side of the tray and is used to heat the heating tank capable of being carried on the tray. Specifically, the tray has a bearing surface and a back surface provided to face away from the bearing surface. The bearing surface of the tray faces the positioning hole to be exposed to the lifting platform 230. The electromagnetic induction coil is disposed on one side of the back surface of the tray, and is located in the hollow lifting platform 230, and is led out of the lifting platform 230 by a cable. Specifically, the tray may be made of an insulating and heat-resistant material. For example, the tray can be made of a non-metallic material, such as nylon.

The electromagnetic induction heating device also includes a weighing sensor, the weighing sensor is disposed below the tray and is configured to measure a weight of the medicinal solution in the heating tank carried on the tray. Both the weighing sensor and the electromagnetic induction coil are electrically coupled to the controller, and the weighing sensor controls the electromagnetic induction coil to be powered on or off through the controller. Certainly, in other embodiments, the weighing sensor may also be omitted, and the electromagnetic induction coil may be controlled to be powered on or off by the touch display. For example, the touch display is provided with physical or virtual switch buttons. When the total amount of medicinal solution in the heating tank meets the requirements, the electromagnetic induction coil can be controlled to be powered on or off by the switch buttons.

Figure 6:
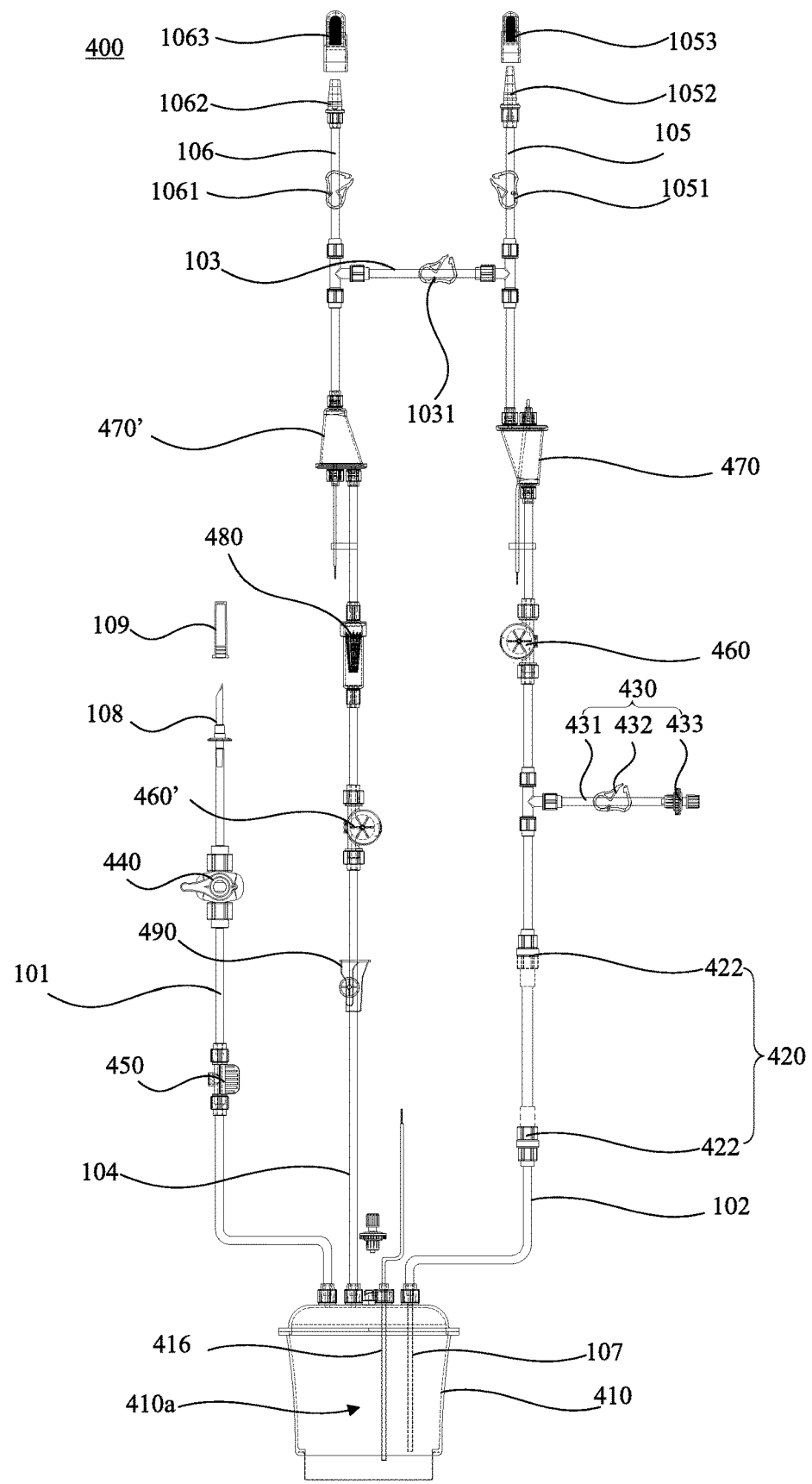
FIG. 6 is a schematic view of a circulation pipeline for hyperthermic perfusion of FIG. 1.
Figure 7:
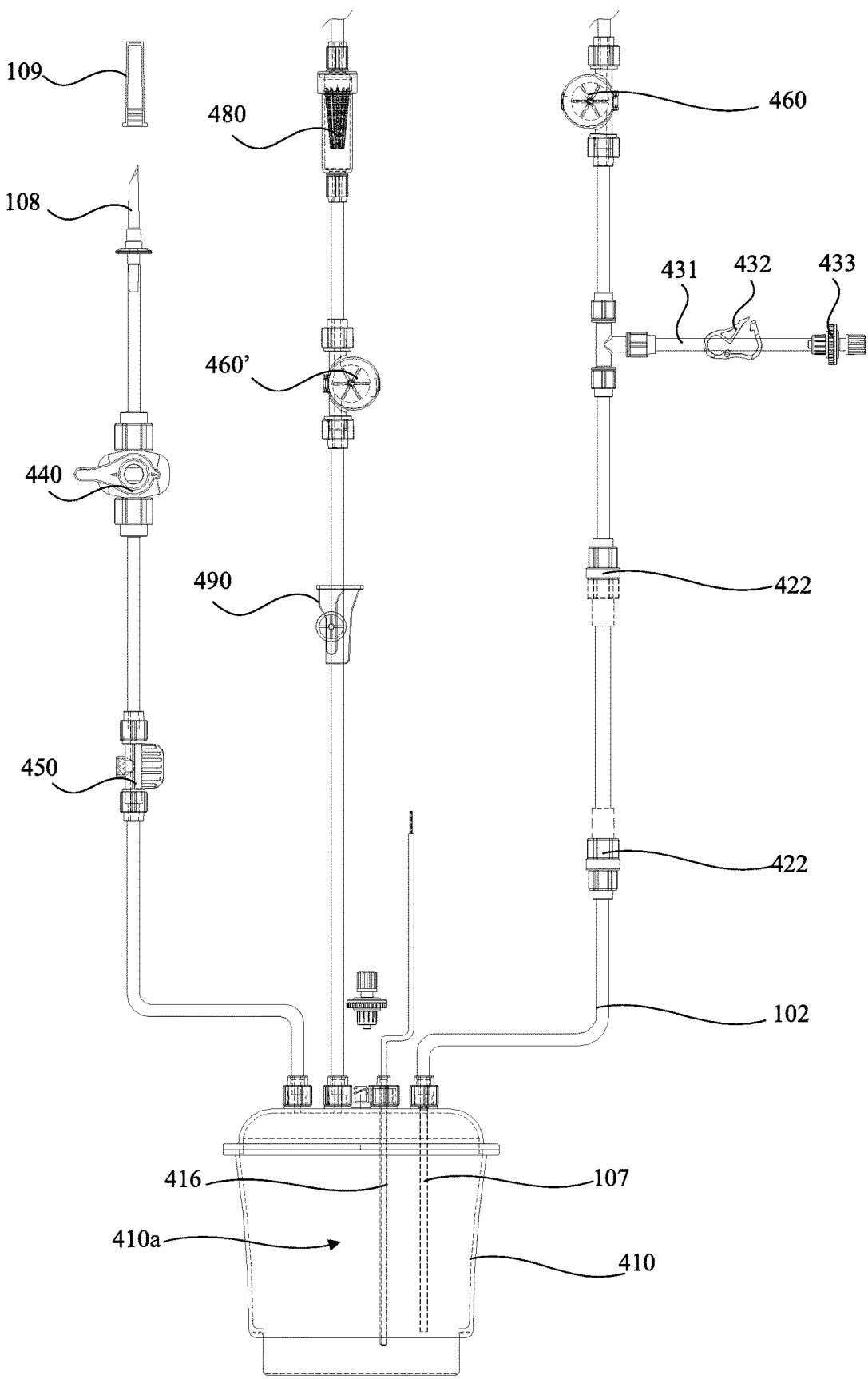
FIG. 7 is a partial schematic view of FIG. 6.
Figure 8:
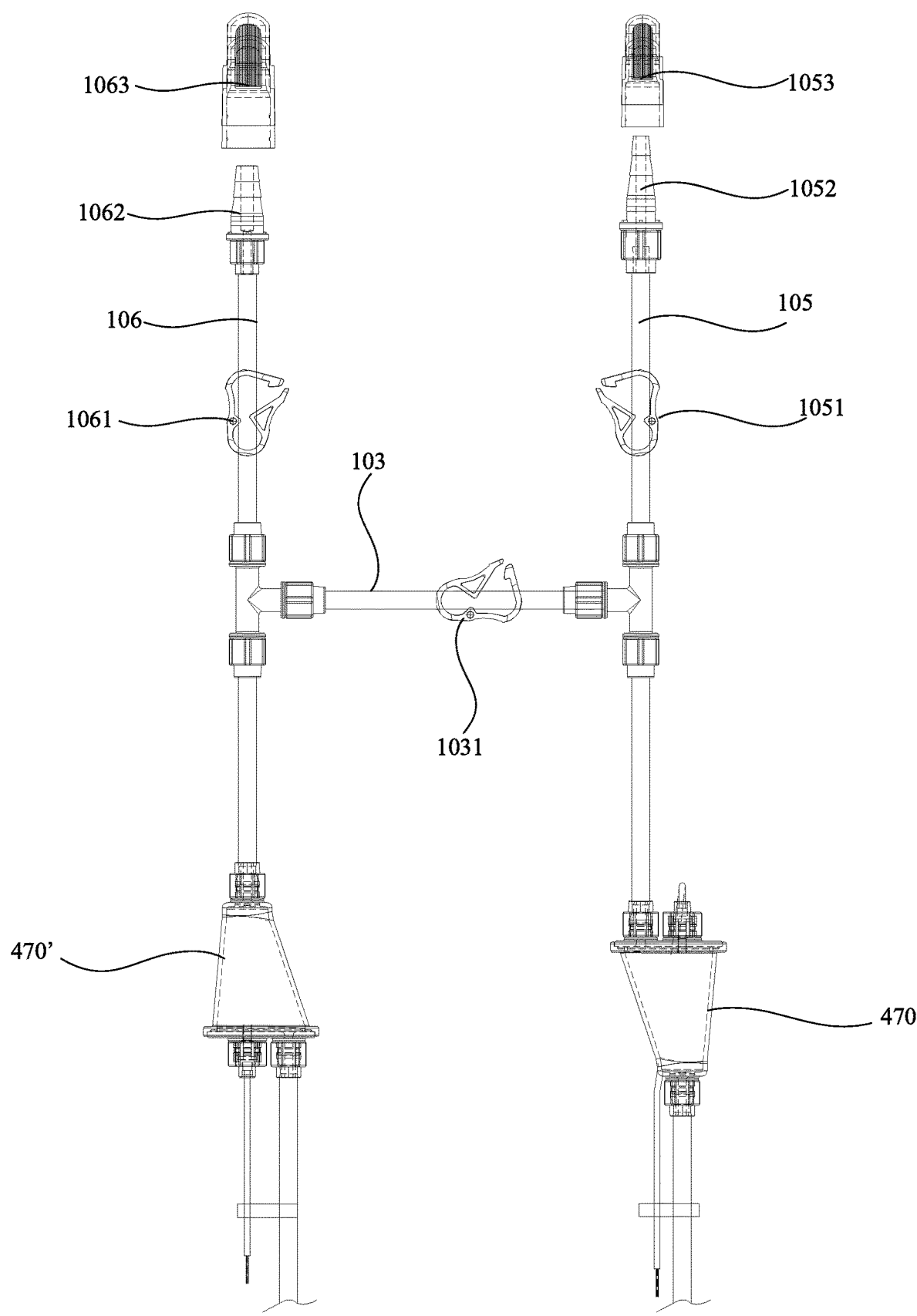
FIG. 8 is another partial schematic view of FIG. 6.

Referring to FIG. 6 to FIG. 8, the circulation pipeline for hyperthermic perfusion 400 includes a heating tank 410, a liquid inlet pipeline 101, a liquid outlet pipeline 102, a circulation pump 420, a cavity inlet pipeline 105, and a cavity outlet pipeline 106 to form a circulation pipeline system, which is connected to a urinary catheter 11' placed in the bladder 10'. Specifically, in the present embodiment, the circulation pipeline for hyperthermic perfusion 400 may further include a pre-filling pipeline 103 to realize that the air in the pipeline system can be exhausted before treatment to avoid causing inflammation. Certainly, in other embodiments, the pre-filling pipeline 103 may be omitted.

Figure 9:
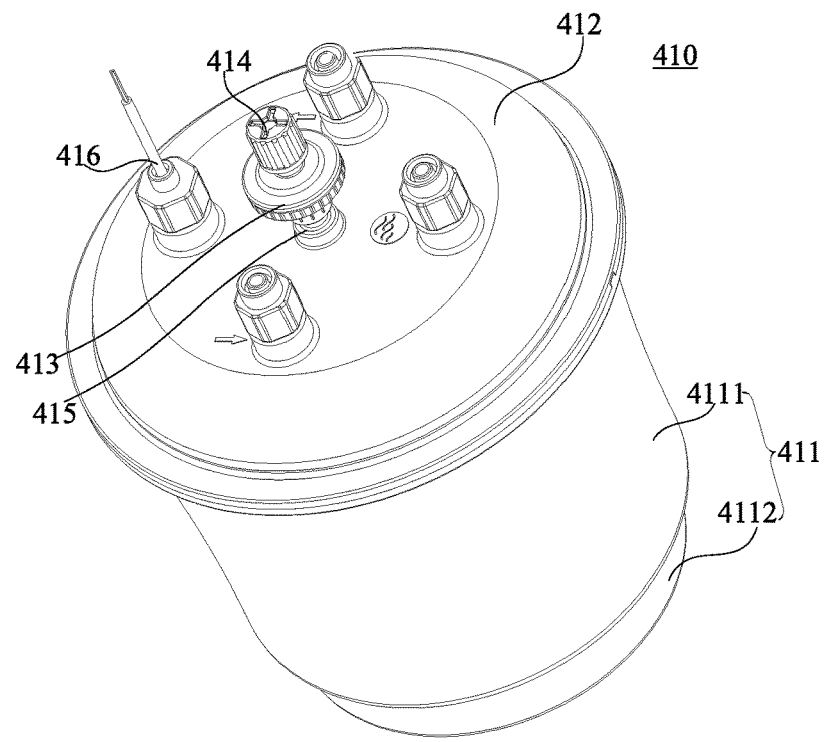
FIG. 9 is a schematic view of a heating tank in accordance with an embodiment.
Figure 10:
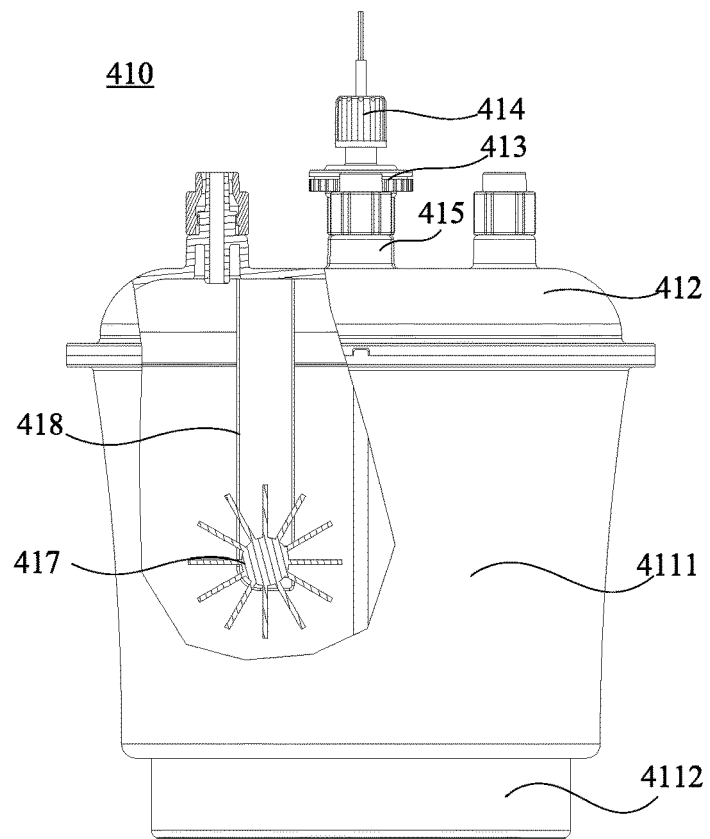
FIG. 10 is a partial sectional view of the heating tank of FIG. 9.
Figure 11:
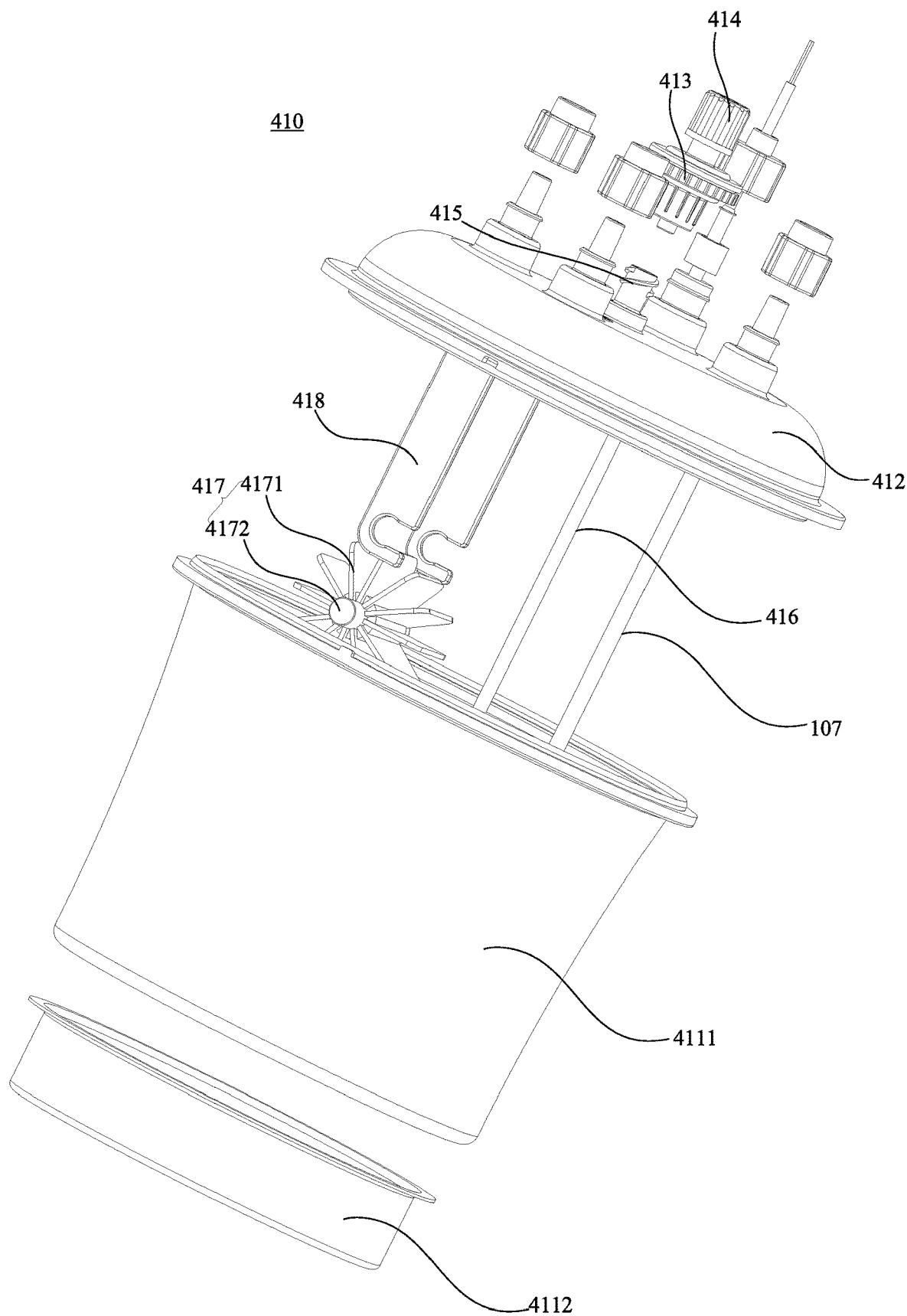
FIG. 11 is an exploded view of the heating tank of FIG. 9.

Referring to FIG. 9 to FIG. 11 together, the heating tank 410 is hollow to form a liquid storage cavity 410a, which is configured to store the medicinal solution. The heating tank 410 is carried on the tray, and the electromagnetic induction coil is used to heat the heating tank 410 to indirectly heat the medicinal solution stored in the liquid storage cavity 410a. One end of the liquid inlet pipeline 101 is in communication with the liquid storage cavity 410a, and the other end of the liquid inlet pipeline 101 is configured to be in communication with a medicinal solution bag 600' (or a medicinal solution bottle, a medicinal solution tank, etc.). One end of the liquid outlet pipeline 102 is in communication with the liquid storage cavity 410a, and the other end of the liquid outlet pipeline 102 is in communication with one end of the pre-filling pipeline 103 and one end of the cavity inlet pipeline 105. The pre-filling pipeline 103 and the cavity inlet pipeline 105 are arranged in parallel. For example, a pipette 107 may be connected in series to one end of the liquid outlet pipeline 102, the pipette 107 extends into the liquid storage cavity 410a, and one end of the pipette 107 is proximate to a bottom of the heating tank 410 to ensure that the medicinal solution in the heating tank 410 can be smoothly extracted into the liquid outlet pipeline 102.

The circulation pump 420 is connected in series to the liquid outlet pipeline 102, and is configured to extract the medicinal solution in the liquid storage cavity 410a. Specifically, the circulation pump 420 includes a roller pump 421 and two pump pipe joints 422. The two pump pipe joints 422 are respectively connected to two opposite ends of the roller pump 421, and are configured to connect the roller pump 421 in series to the liquid outlet pipeline 102. The roller pump 421 is configured to adjust a speed of extracting liquid from the heating tank 410.

One end of the pre-filling pipeline 103 is in communication with the other end of the liquid outlet pipeline 102, and the other end of the pre-filling pipeline 103 is in communication with one end of the liquid return pipeline 104. The pre-filling pipeline 103 is connected in parallel with both the cavity inlet pipeline 105 and the cavity outlet pipeline 106. A pre-filling valve 1031 is also connected in series to the pre-filling pipeline 103 and is configured to control opening and closing of the pre-filling pipeline 103. One end of the liquid return pipeline 104 is in communication with the other end of the pre-filling pipeline 103 and the other end of the cavity outlet pipeline 106, and the other end of the liquid return pipeline 104 is in communication with the liquid storage cavity 410a. The liquid return pipeline 104 is capable of allowing the medicinal solution in the bladder 10' discharged through the cavity outlet pipeline 106 to flow back to the heating tank 410. For example, the liquid return pipeline 104, the pre-filling pipeline 103, and the cavity outlet pipeline 106 may be connected together through a T-pipe.

One end of the cavity inlet pipeline 105 is in communication with the other end of the liquid outlet pipeline 102, and the other end of the cavity inlet pipeline 105 is configured to be in communication with the body cavity (the bladder 10' in the present embodiment). The cavity inlet pipeline 105 is capable of introducing the medicinal solution into the bladder 10'. Specifically, a cavity inlet valve 1051 may be connected in series to the cavity inlet pipeline 105 to control the opening and closing of the cavity inlet pipeline 105. A cavity inlet conical head 1052 can also be provided on the other end of the cavity inlet pipeline 105 to facilitate cooperation with the urinary catheter 11'. Optionally, a protection cap 1053 can also be sleeved on the cavity inlet conical head 1052, and is configured to protect the cavity inlet conical head 1052 when not in use, thereby preventing foreign dust or debris from entering the cavity inlet pipeline 105.

One end of the cavity outlet pipeline 106 is configured to be in communication with the body cavity (the bladder 10' in the present embodiment), and the other end of the cavity outlet pipeline 106 is in communication with the liquid return pipeline 104. The pre-filling pipeline 103 is connected in parallel with the cavity inlet pipeline 105 and the cavity outlet pipeline 106. The medicinal solution in the bladder 10' can be discharged by the cavity outlet pipeline 106, and flowed back to the heating tank 410 through the liquid return pipeline 104. Specifically, a cavity outlet valve 1061 may be connected in series to the cavity outlet pipeline 106, and is configured to control opening and closing of the cavity outlet pipeline 106. A cavity outlet conical head 1062 can also be provided on one end of the cavity outlet pipeline 106 to facilitate cooperation with the urinary catheter 11'. Optionally, a protection cap 1063 can also be sleeved on the cavity outlet conical head 1062, and is configured to protect the cavity outlet conical head 1062 when not in use, thereby preventing foreign dust or debris from entering the cavity outlet pipeline 106.

The heating tank 410 is a non-deformable tank. The heating tank 410 includes a tank body 411 and a cover body 412. The tank body 411 is hollow, and one end of the tank body 411 is opened to form an open end. The cover body 412 is disposed on the open end of the tank body 411. The cover body 412 and the tank body 411 together form the liquid storage cavity 410a that is configured to store liquid. During use, the tank body 411 is configured to be placed on the electromagnetic induction heating device, and the electromagnetic induction heating device is configured to heat the tank body 411 to indirectly heat the liquid in the liquid storage cavity 410a, so that a non-direct contact heating method is achieved, the medicinal solution can be prevented from being polluted, thereby meeting the aseptic requirements.

Specifically, in the present embodiment, the tank body 411 includes a tank shell 4111 and a base 4112. The base 4112 is disposed on the bottom of the tank body 411. The tank shell 4111 is made of plastic materials, and the base 4112 is made of metal materials. The base 4112 and the tank shell 4111 are integrally formed by an injection molding. Therefore, the entire heating tank 410 has a low manufacturing cost and a simple manufacturing process, and is convenient to use as a disposable product. When an electromagnetic induction coil is energized, only the bottom of the heating tank 410 is heated, and the liquid in the heating tank 410 is uniformly heated by utilizing the natural convection action of the liquid in the heating tank 410. For example, the base 4112 may be made of medical grade 304 stainless steel.

Certainly, in other embodiments, the tank body 411 has the bottom, which is away from the open end. Only the bottom of the tank body 411 is made of metal materials, and the rest of the tank body 411 is made of plastic materials. Alternatively, the tank body 411 may be integrally made of metal materials. Therefore, when the electromagnetic induction coil is energized to heat the heating tank 410, the liquid in the heating tank 410 is heated indirectly.

Specifically, in the present embodiment, the heating tank 410 further includes an air filter 413 and a sealing cap 414. A matching joint 415 is formed on the cover body 412, and the air filter 413 is in communication with the liquid storage cavity 410a through the matching joint 415. The sealing cap 414 is capable of sealing the air filter 413. The air filter 413 is mainly used to prevent bacteria or particles in the air from directly entering the liquid storage cavity 410a to cause the contamination of the medical solution when the air pressure in the tank body 411 is in communication with the atmospheric pressure. Specifically, the air filter 413 includes a multilayer air filter element for filtering external air to prevent the bacteria carried in the air from entering the liquid storage cavity 410a. For example, the air filter 413 includes a casing made of ABS and AS materials, and a filter membrane made of PP and PTFE materials. A filtration rate of 0.5 micron particles in the air with the air filter 413 is greater than 90%.

Specifically, the air filter 413 is connected to the matching joint 415 by a threaded engagement. The air filter 413 is provided with a through-hole. The air filter element is located in the through-hole. The sealing cap 414 is rotatably disposed on the air filter 413 and can seal the through-hole. The sealing cap 414 is mainly used to adjust the pressure in the liquid storage cavity 410a. Since the tank body 411 is made of a non-deformable material, when the volume of the medicinal solution in the tank body 411 is changed, the pressure in the tank body 411 is changed. For example, when the medicinal solution is injected into the heating tank 410, the pressure in the tank body 411 increases with the increase of the medicinal solution, which may eventually cause the pressure in the tank body 411 to be equal to the pressure for injecting the medicinal solution, so that no more medicinal solution can be injected. Alternatively, when the tank body 411 is fully loaded, a negative pressure may be generated in the liquid storage cavity 410a after the medicinal solution in the liquid storage cavity 410a is extracted. At this time, the medicinal solution in the bladder 10' can be sucked out by adjusting the negative pressure.

Specifically, in the present embodiment, the heating tank 410 further includes a first temperature measuring assembly 416, which is used to accurately measure the temperature of the liquid in the liquid storage cavity 410a to monitor the temperature of the liquid in real time. The first temperature measuring assembly 416 includes a first temperature sensor and a first hollow pipe. The first temperature sensor has a first probe end extending into the first hollow pipe and located on an end of the first hollow pipe. One end of the first hollow pipe extends into the liquid storage cavity 410a and is disposed proximate to the bottom of the tank body 411. Therefore, the first temperature measuring assembly 416 can always be in contact with the liquid to ensure that the actual temperature of the liquid is measured, rather than the temperature of the air leaving the liquid level. However, there is a certain distance between the end of the first temperature measuring assembly 416 and the bottom of the tank body 411, so that the phenomenon that the first temperature measuring assembly 416 generates heat or is interfered by the electromagnetic induction heating device to cause inaccurate measurement is avoided.

The heating tank 410 further includes a stirring impeller 417, which is located in the liquid storage cavity 410a and below the liquid return pipeline 104, and is capable of rotating under the action of the liquid flowing back to the liquid storage cavity 410a through the liquid return pipeline 104. Specifically, the stirring impeller 417 is disposed on a side of the cover body 412 facing the tank body 411 by a support frame 418. The stirring impeller 417 includes a stirring blade 4171 and a rotating shaft 4172. Both ends of the rotating shaft 4172 are rotatably disposed on the support frame 418, and the stirring blade 4171 is fixed on the rotating shaft 4172. Certainly, in other embodiments, the rotating shaft 4172 may also be fixed on the support frame 418, and the stirring blade 4171 may rotate relative to the rotating shaft 4172.

When the liquid storage cavity 410a is filled with liquid, the electromagnetic induction heating device indirectly heats the liquid through the tank body of the heating tank 410. Because the base 4112 of the tank body 411 or the bottom of the tank body 411 is made of stainless steel, the heat is transferred to the liquid from the bottom of the tank body 411. The density of the liquid decreases after the liquid is heated, the liquid will naturally float upwards, while the liquid with a low temperature above will sink, thereby resulting in a natural convection process. In this process, the stirring impeller 417 is also rotated, thereby playing a role of stirring.

Referring to FIG. 1, FIG. 6, and FIG. 7 again, the circulation pipeline for hyperthermic perfusion 400 further includes a pressure measuring assembly 430, which is connected in series to the liquid outlet pipeline 102 and is located behind a station of the circulation pump 420. The pressure measuring assembly 430 is configured to measure a pressure in the liquid outlet pipeline 102 behind the station of the circulation pump 420, so that the pressure in the liquid outlet pipeline 102 can be monitored, which may avoid the damage to the bladder 10' caused by the excessive pressure, or avoid that the medicinal solution cannot enter the bladder 10' due to the too little pressure.

Specifically, the pressure measuring assembly 430 includes a pressure measuring extension pipe 431, a pressure measuring valve 432, and a pressure measuring protection cap 433. The pressure measuring extension pipe 431 is connected in series to the liquid outlet pipeline 102 and is located behind the station of the circulation pump 420. The pressure measuring valve 432 is configured to control opening and closing of the pressure measuring extension pipe 431, and the pressure measuring protection cap 433 is sleeved on one end of the pressure measuring extension pipe 431. The pressure of the medicinal solution flowing out of the circulation pump 420 in the liquid outlet pipeline 102 can be monitored in real time by externally connecting the pressure measuring extension pipe 431 to the pressure measuring sensor.

One end of the liquid inlet pipeline 101, which is configured to be in communication with the medicinal solution bag, is provided with a contact pin 108. The contact pin 108 is used to be inserted into the medicinal solution bag to smoothly introduce the medicinal solution in the medicinal solution bag into the liquid inlet pipeline 101. Optionally, a protection cover 109 can also be sleeved on the contact pin 108 to cover the contact pin 180, which not only prevents the contact pin 108 from accidentally damaging the operator, but also prevents external debris and dust from entering the liquid inlet pipeline 101 through the contact pin.

Figure 12:
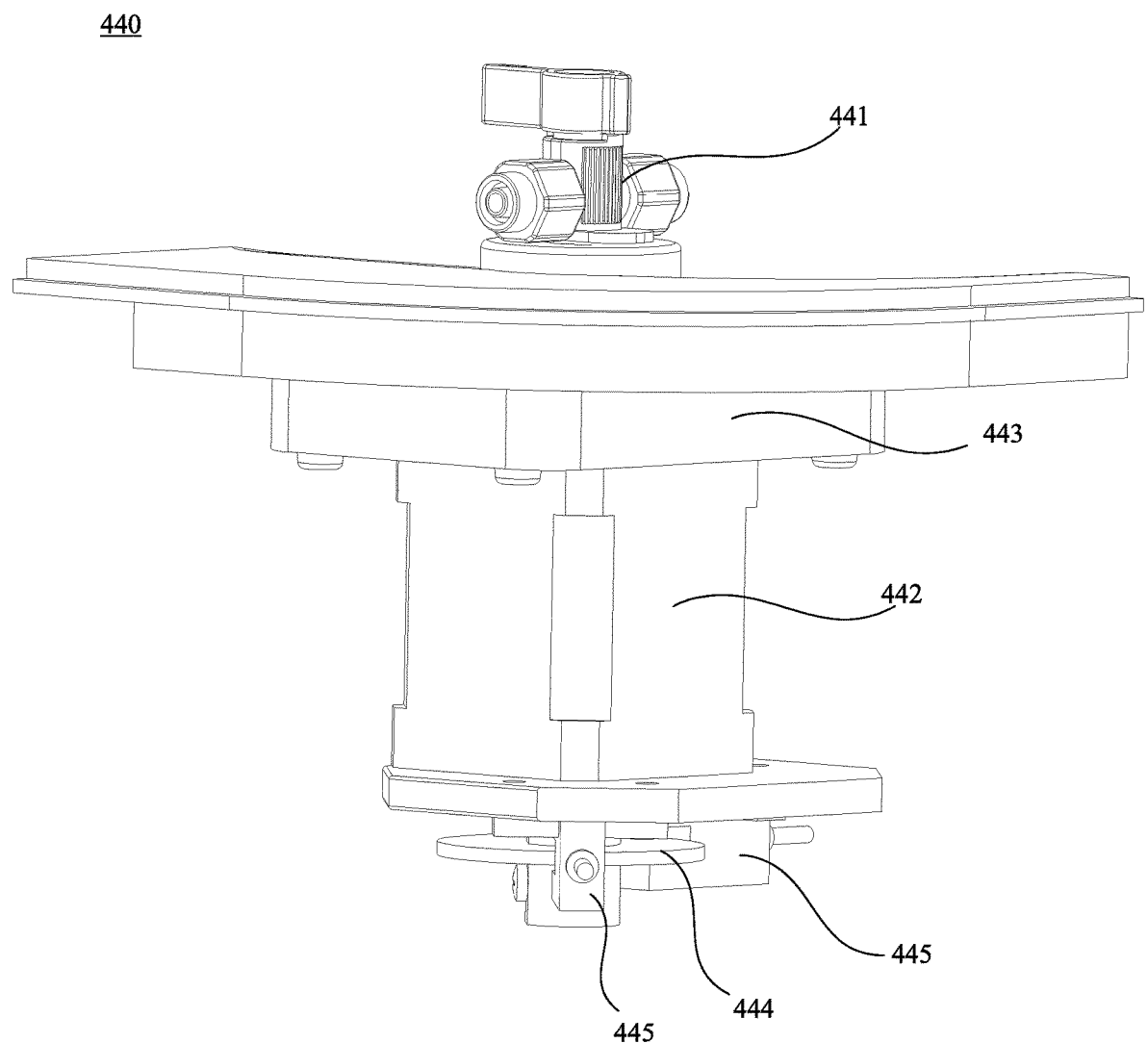
FIG. 12 is a schematic view of a two-way valve in accordance with an embodiment.
Figure 13:
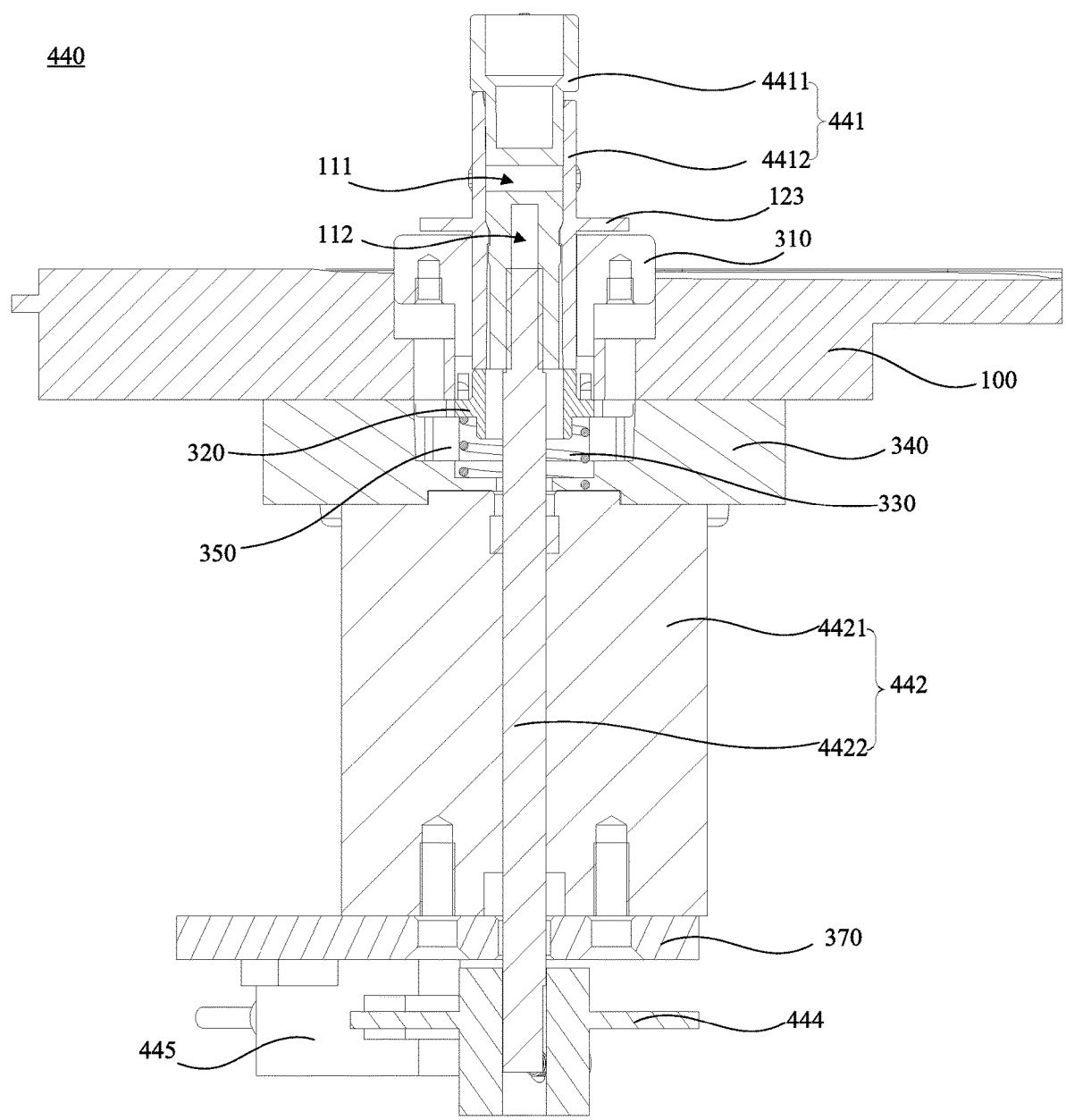
FIG. 13 is a sectional view of the two-way valve of FIG. 12.
Figure 14:
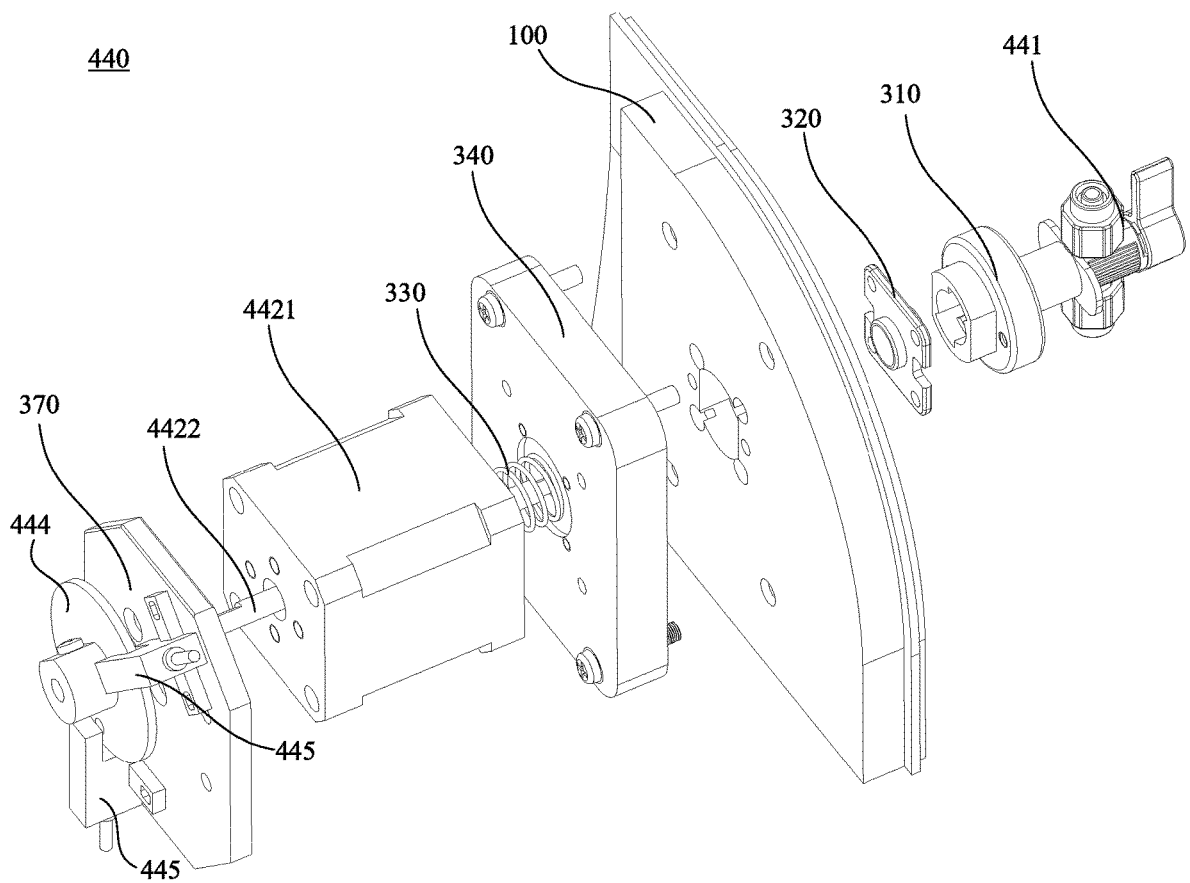
FIG. 14 is a schematic exploded view of the two-way valve of FIG. 12.
Figure 15:
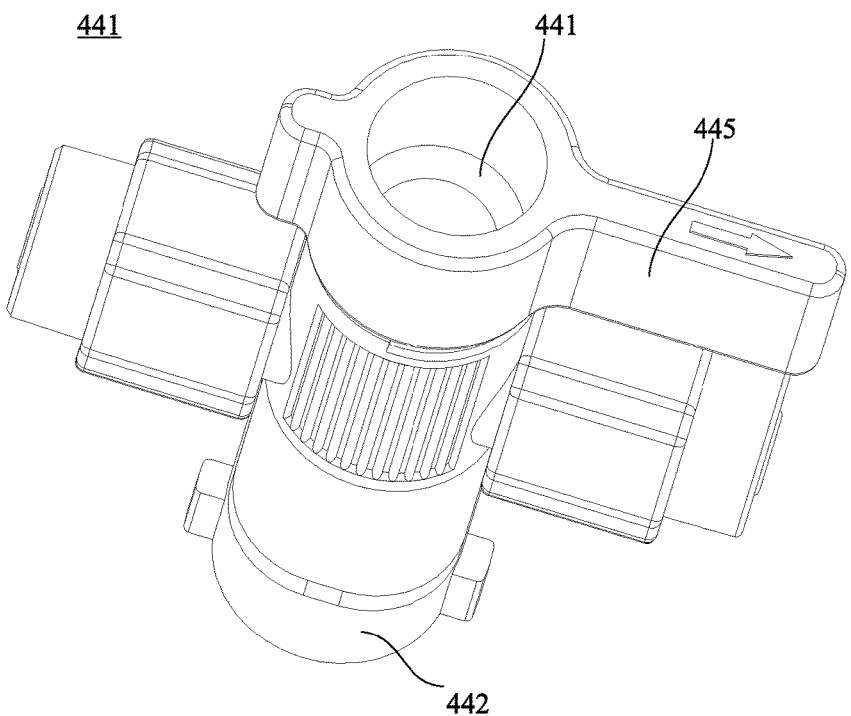
FIG. 15 is a schematic view of a valve main body of FIG. 12.
Figure 16:
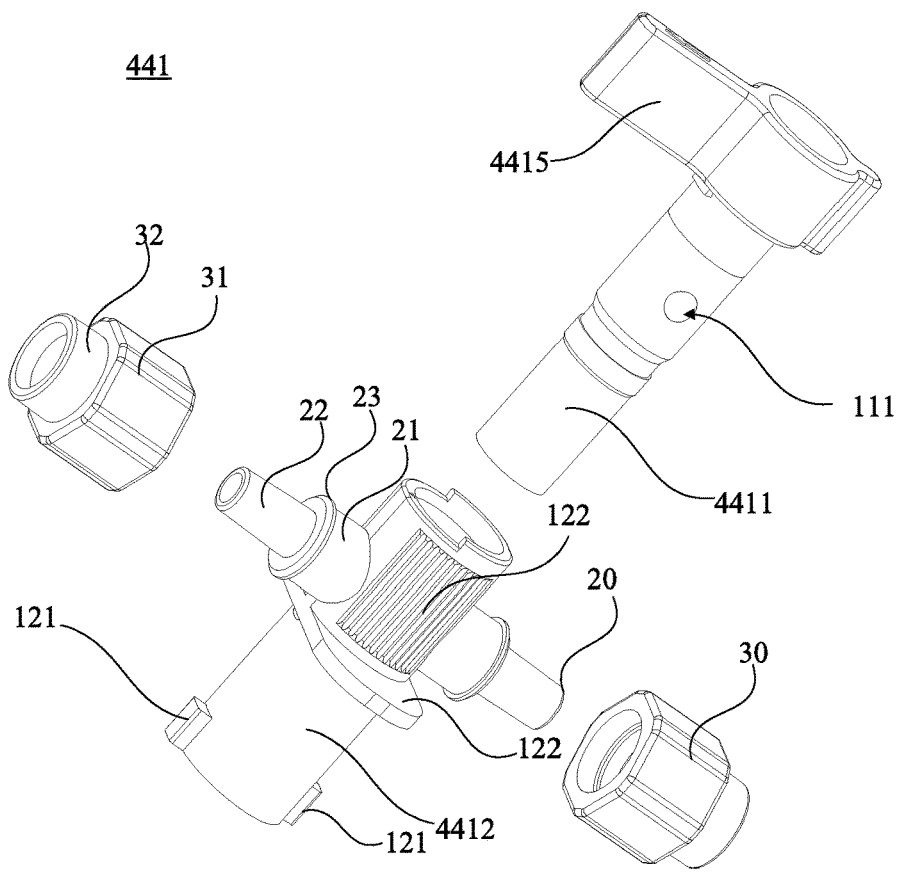
FIG. 16 is a schematic exploded view of the valve main body of FIG. 15.
Figure 17:
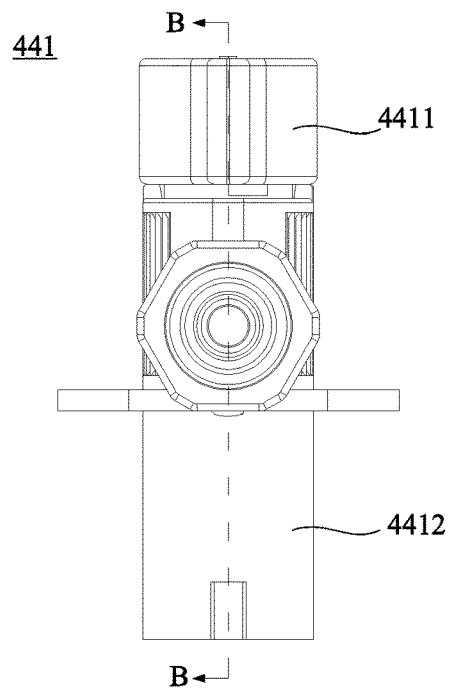
FIG. 17 is a schematic view of the valve main body of FIG. 15 with another perspective.
Figure 18:
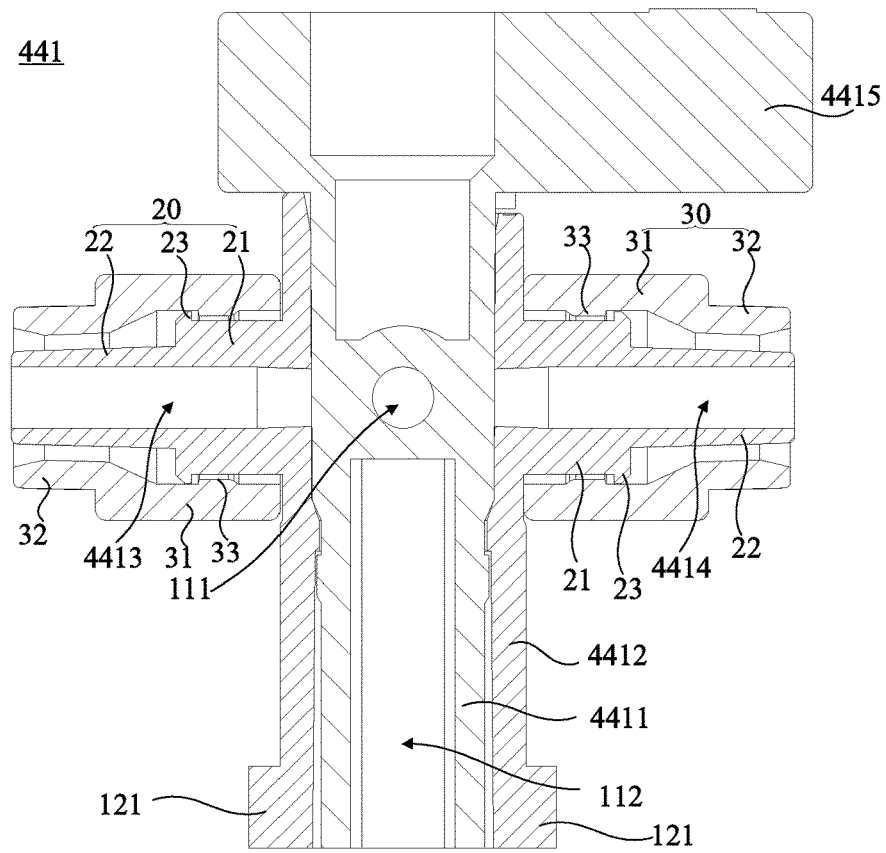
FIG. 18 is a sectional view taken along a line B-B in FIG. 17.

Referring to FIG. 12 to FIG. 14, the circulation pipeline for hyperthermic perfusion 400 further includes a two-way valve 440. The two-way valve 440 is connected in series to the liquid inlet pipeline 101 and is configured to control opening and closing of the liquid inlet pipeline 101. Specifically, the two-way valve 440 can realize the opening and closing of the liquid inlet pipeline 101 by an automatic control manner. Referring to FIG. 15 to FIG. 18, the two-way valve 440 includes a valve main body 441 including a valve core 4411 and a valve body 4412. The valve core 4411 is provided with a liquid through hole 111. At least one end of the valve body 4412 is opened and an interior of the valve body 4412 is hollow to form a receiving cavity. A first liquid inlet channel 4413 and a first liquid outlet channel 4414 which are in communication with the receiving cavity are formed on a side wall of the valve body 4412. One end of the valve core 4411 extends into the receiving cavity, and is rotatable relative to the valve body 4412, so that the liquid through hole 111 can be or cannot be in communication with the first liquid inlet channel 4413 and the first liquid outlet channel 4414.

The valve core 4411 is also provided with a blind hole 112, and the liquid through hole 111 and the blind hole 112 are not in communication with each other. For example, the liquid through hole 111 extends in a radial direction of the valve core 4411, and the blind hole 112 extends in an axial direction of the valve core 4411. A barrier wall is provided between the liquid through hole 111 and the blind hole 112 to prevent the liquid through hole 111 from being in communication with the blind hole 112, so that liquid leakage is avoided. The valve core 4411 has a substantially cylindrical shape, and the receiving cavity is substantially a circular hole, which may facilitate the rotation of the valve core 4411 in the receiving cavity. Certainly, in other embodiments, the liquid through hole 111 may not only be limited to extend in the radial direction, but may also be a curved through hole or the like, for example, as long as the liquid through hole 111 can allow the liquid to circulate and is not in communication with the blind hole 112.

When the liquid through hole 111 is opposite to the first liquid inlet channel 4413 and the first liquid outlet channel 4414, the two-way valve 440 is in a communication state. When the liquid through hole 111 is staggered from the first liquid inlet channel 4413 and the first liquid outlet channel 4414, the two-way valve 440 is in a non-communication (i.e. disconnected) state. The valve core 4411 and the valve body 4412 are in an interference fit to prevent leakage.

Specifically, in the present embodiment, an outer side wall of the end of the valve core 4411 extending into the receiving cavity wall is recessed to form a positioning groove, and an inner side wall of the receiving cavity protrudes to form a positioning convex ring matched with the positioning groove. Therefore, the positions of the valve core 4411 and the valve body 4412 can be positioned by the matching of the positioning groove with the positioning convex ring, which may prevent the valve core 4411 from excessively extending into the valve body 4412.

Specifically, in the present embodiment, the other end of the valve core 4411 extends out of the receiving cavity, and the other end of the valve core 4411 protrudes to form an operation handle 4415. The operation handle 4415 can be operated manually to rotate the valve core 4411 relative to the valve body 4412, which prevents a situation where the valve core 4411 cannot be rotated due to the failure of the automatic control method.

Referring to FIGS. 12 to 14 again, the two-way valve 440 further includes a driving mechanism 442 and a mounting mechanism 443. The mounting mechanism 443 is used to mount the valve body 441. The driving mechanism 442 can automatically drive the valve core 4411 to rotate relative to the valve body 4412, thereby realizing the opening and closing of the liquid inlet pipeline 101. The driving mechanism 442 includes a second driving source 4421 and a driving shaft 4422. The second driving source 4421 is used to drive the driving shaft 4422 to rotate. One end of the driving shaft 4422 extends into the blind hole 112, and the driving shaft 4422 can drive the valve core 4411 to rotate relative to the valve body 4412. Specifically, the second driving source 4421 may be a motor. The driving shaft 4422 can be an in-line shaft, and the blind hole 112 can be an in-line hole, so that it can be ensured that the rotation of the driving shaft 4422 can drive the valve core 4411 to rotate without relative sliding. Certainly, in other embodiments, the driving shaft 4422 and the blind hole 112 may also be other shapes, as long as the purpose that the rotation of the valve shaft 4422 can drive the valve core 4411 to rotate without relative sliding can be achieved. The second driving source 4421 is electrically coupled to the controller. The controller controls the second driving source 4421 to drive the driving shaft 4422 to rotate for driving the valve core 4411 to rotate relative to the valve body 4412.

Figure 19:
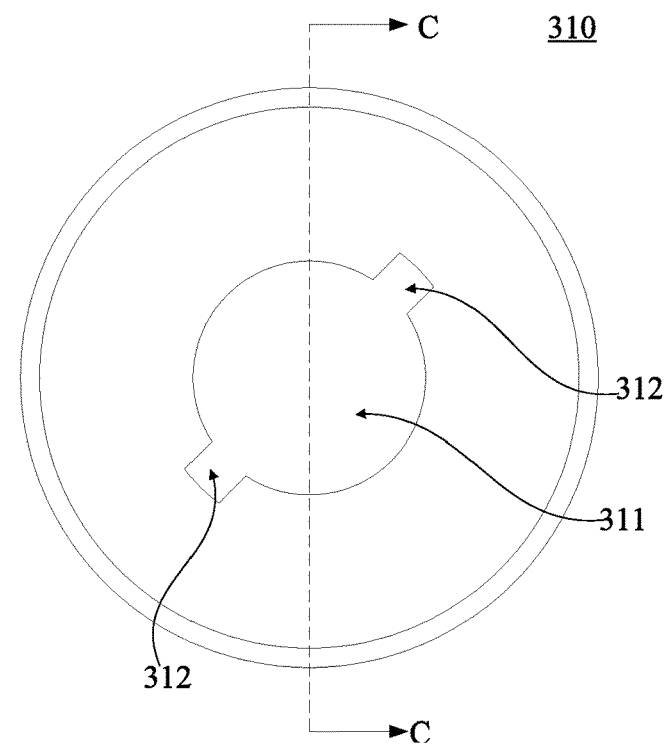
FIG. 19 is a top view of a mounting base of FIG. 14.
Figure 20:
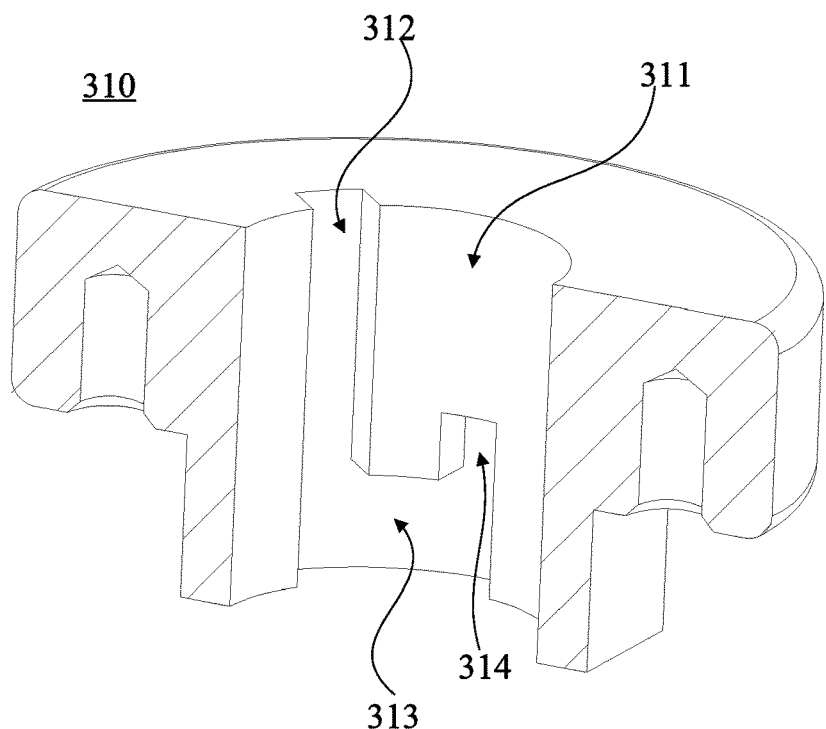
FIG. 20 is a sectional view taken along a line C-C in FIG. 19.

The mounting mechanism 443 includes a mounting base 310, a supporting plate 320, a spring 330, a first mounting plate 340, a guide post 350, and a second mounting plate 370. Referring to FIG. 19 and FIG. 20, the mounting base 310 is provided with a through hole 311 that penetrates two opposite ends of the mounting base 310. The through hole 311 is provided with a guide groove 312, a communicating groove 313, and a limiting groove 314 at an inner wall thereof. The guide groove 312 extends along an axial direction of the mounting base 310 and penetrates at least one end surface of the mounting base 310. The communicating groove 313 is in communication with the guide groove 312 and the limiting groove 314.

For example, in the present embodiment, the guide groove 312 penetrates the opposite end surfaces of the mounting base 310, so that the guide groove 312 is a through groove, and one end of the valve body 4412 can penetrate the mounting base 310 through the guide groove 312. The communicating groove 313 penetrates one of the end surfaces of the mounting base 310, and the one of the end surfaces is the end surface of the mounting base 310 facing the supporting plate 320. The limiting groove 314 also penetrates one of the end surfaces of the mounting base 310, and the one of the end surfaces is the end surface of the mounting base 310 facing the supporting plate 320. The limiting groove 314 does not penetrate the end surface of the mounting base 310 facing the valve core 4411 to play a role of limiting.

Certainly, in other embodiments, the guide groove 312 may penetrate only one of the end surfaces of the mounting base 310, and the one of the end surfaces is the end surface facing the valve core 4411. At this time, neither the communicating groove 313 nor the limiting groove 314 penetrates the end surface of the mounting base 310.

An outer side wall of one end of the valve body 4412 protrudes to form a positioning block 121 extending along an axial direction of the valve body 4412. The positioning block 121 can extend from the guide groove 312 into the mounting base 310 and move into the limiting groove 314 through the communicating groove 313. Specifically, in the present embodiment, the number of the positioning blocks 121 is two, and the two positioning blocks 121 are oppositely disposed on the outer side wall of the valve body 4412 at intervals. Correspondingly, the number of the guide grooves 312, the communicating grooves 313, and the limiting grooves 314 is also two, and one positioning block 121 corresponds to one guide groove 312, one communicating groove 313, and one limiting groove 314. For example, the two positioning blocks 121 are separated by 180 degrees. Similarly, the two guide grooves 312 are also separated by 180 degrees, the two communicating grooves 313 are also separated by 180 degrees, the two limiting grooves 314 are also separated by 180 degrees. The guide groove 312 and the limiting groove 314 are separated by 45 degrees. Therefore, during assembling, the valve body 4412 is inserted into the guide groove 312 of the mounting base 310 through the positioning block 121, and the positioning block 121 matches with the guide groove 312 to play a role of guiding.

The two positioning blocks 121 are different in size, so that it can effectively play a fool-proof role and avoid errors during assembly. An outer side wall of the positioning block 121 facing away from the valve body 4412 is a tapered surface, so that it can better match with the guide groove 312 to better play a role of guiding. During assembly, the positioning block 121 is inserted into the mounting base 310 through the guide groove 312, and then moves along the communicating groove 313 into the limiting groove 314, and is restricted in the limiting groove 314. The positioning block 121 plays a role of a snap-action.

Specifically, in the present embodiment, the valve body 4412 is formed with an antiskid texture 122 on the outer side wall thereof, so that a friction between the hand and the valve body 4412 can be increased during assembly. The outer side wall of the valve body 4412 protrudes to form a positioning baffle 123. Therefore, during assembly, the positioning baffle 123 is mainly used to position the hand. In addition, the valve body 4412 needs to be pressed downwards during assembly, so that the positioning baffle 123 can provide a pressing stress surface, and the assembly is convenient.

The supporting plate 320 is located between the mounting base 310 and the spring 330. One end of the driving shaft 4422 passes through the supporting plate 320 and the through hole 311 of the mounting base 310, and extends into the blind hole 112. The spring 330 is sleeved on the driving shaft 4422, and one end of the spring 330 abuts against the supporting plate 320, and the other end of the spring 330 abuts against the second driving source 4421.

The first mounting plate 340 is provided with a first through hole that penetrates two opposite sides of the first mounting plate 340, and one end of the driving shaft 4422 and one end of the spring 330 pass through the first through hole. The second driving source 4421 is mounted on the first mounting plate 340, and the supporting plate 320 is located between the first mounting plate 340 and the mounting base 310. The first through hole may be a stepped hole, and the supporting plate 320 can move reciprocally in the stepped hole under the action of an elastic force of the spring 330.

The supporting plate 320 is provided with at least two first guide holes. A second guide hole is formed on one side of the first mounting plate 340 facing the supporting plate 320. The guide post 350 is provided in and sequentially passes through the first guide holes and the second guide hole. The guide post 350 is provided to ensure that the supporting plate 320 moves reciprocally along the axial direction to prevent the supporting plate 320, the mounting base 310, the valve body 4412, and the valve core 4411 from shaking. For example, the number of the first guide holes may be four, and the first guide holes are respectively distributed at four corners of the supporting plate 320. Correspondingly, the number of the guide posts 350 and the second guide holes are four. The guide posts 350 and the second guide holes are matched with the first guide holes.

The housing 100 is provided with a second through hole that penetrates two opposite sides of the housing 100. The housing 100 is located between the mounting base 310 and the first mounting plate 340, and the first mounting plate 340 is fixed on the housing 100. Therefore, the whole management system can have a fixed point during use to prevent the pipeline system from shaking. The second through hole may be a stepped hole. Correspondingly, the mounting base 310 may be a circular boss structure matched with the stepped hole.

The second mounting plate 370 and the first mounting plate 340 are respectively located at two opposite ends of the second driving source 4421, and the two-way valve 440 further includes an indexing positioner 444 and two photoelectric switches 445 disposed at intervals. The two photoelectric switches 445 are mounted on the second mounting plate 370. The indexing positioner 444 is provided with three positioning holes and is disposed at the other end of the driving shaft 4422. The indexing positioner 444 rotates relative to the photoelectric switch along with the rotation of the driving shaft 4422. The photoelectric switch 445 is electrically coupled to the controller, so that the actual position of the two-way valve 440 can be determined by the two photoelectric switches 445 and can be fed back to the controller in real time.

Figure 21:
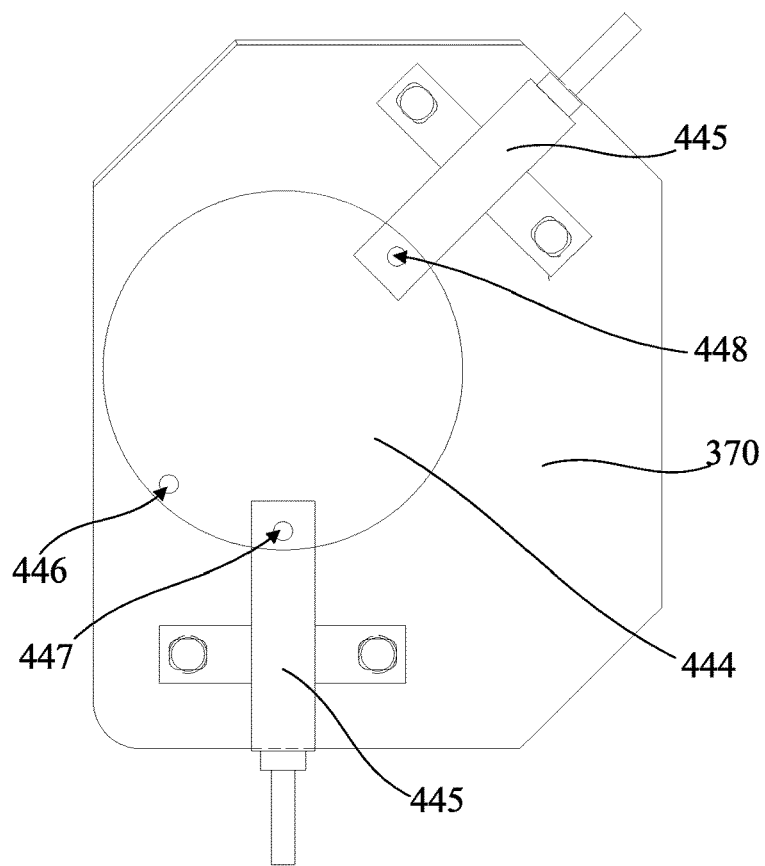
FIG. 21 is a schematic view illustrating a second mounting plate, an indexing positioner, and a photoelectric switch in accordance with an embodiment where the two-way valve is in an initial state.
Figure 22:
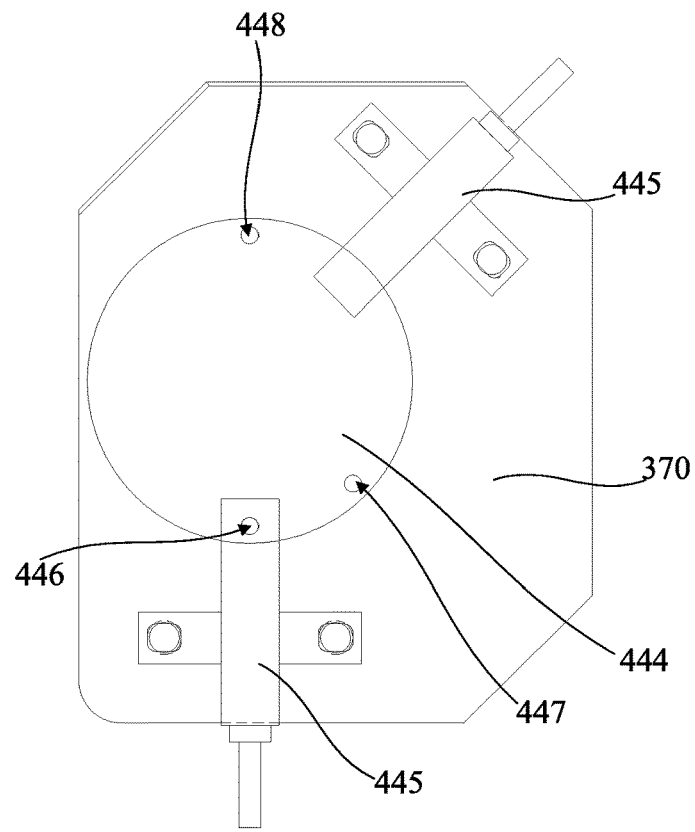
FIG. 22 is a schematic view illustrating the second mounting plate, the indexing positioner, and the photoelectric switch of FIG. 21 where the two-way valve is in a non-communication state.
Figure 23:
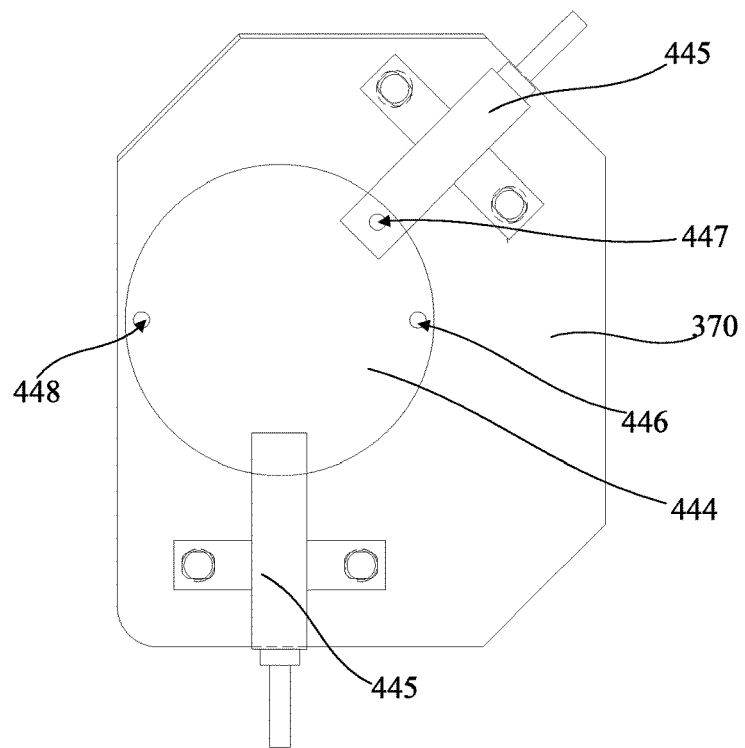
FIG. 23 is a schematic view illustrating the second mounting plate, the indexing positioner, and the photoelectric switch of FIG. 21 where the two-way valve is in a communication state.

Referring to FIG. 21 to FIG. 23, specifically, in the present embodiment, the three positioning holes are a first positioning hole 446, a second positioning hole 447, and a third positioning hole 448, respectively. The first positioning hole 446 is separated from the third positioning hole 448 by 180 degrees, the first positioning hole 446 is separated from the second positioning hole 447 by 45 degrees, and the second positioning hole 447 is separated from the third positioning hole 448 by 135 degrees. The two photoelectric switches 445 are separated by 135 degrees. When any positioning hole is located directly below the photoelectric switch 445, the photoelectric switch 445 outputs 1; otherwise, the photoelectric switch 445 outputs 0.

One end of the valve core 4411 extends into the receiving cavity of the valve body 4412 until the positioning groove matches with the positioning convex ring. At this time, the liquid through hole 111 is not in communication with the first liquid inlet channel 4413 and the first liquid outlet channel 4415. Then, the valve body 4412 is pressed, the valve body 4412 presses the supporting plate 320, the supporting plate 320 presses the spring 330 to compress the spring 330. One end of the valve body 4412 extends into the through hole 311, and the positioning block 121 moves in the guide groove 312. At this time, the two-way valve 440 is in the initial position, which corresponds to the state shown in FIG. 21, where the second positioning hole 447 and the third positioning hole 448 are located directly below the photoelectric switches 445. The states output by the two photoelectric switches 445 are "11".

When the communicating groove 313 is reached, the valve body 4412 is rotated clockwise by 45 degrees. At this time, the positioning block 121 moves from the guide groove 312 into the limiting groove 314 through the communicating groove 313, and then the valve body 4412 is released, the valve body 4412 and the supporting plate 320 are limited in the limiting groove 314 by a restoring force of the spring 330. At this time, only the first positioning hole 446 is located directly below the photoelectric switch 445, and the states output by the two photoelectric switches 445 are "10".

When the second drive source 4421 drives the valve core 4411 to continue to rotate clockwise by 90 degrees, the second positioning hole 447 is located directly below the photoelectric switch 445, and the states output by the two photoelectric switches 445 are "01". Therefore, the actual position of the two-way valve 440 can be determined by the two photoelectric switches 445 and can be fed back to the controller in real time.

Figure 24:
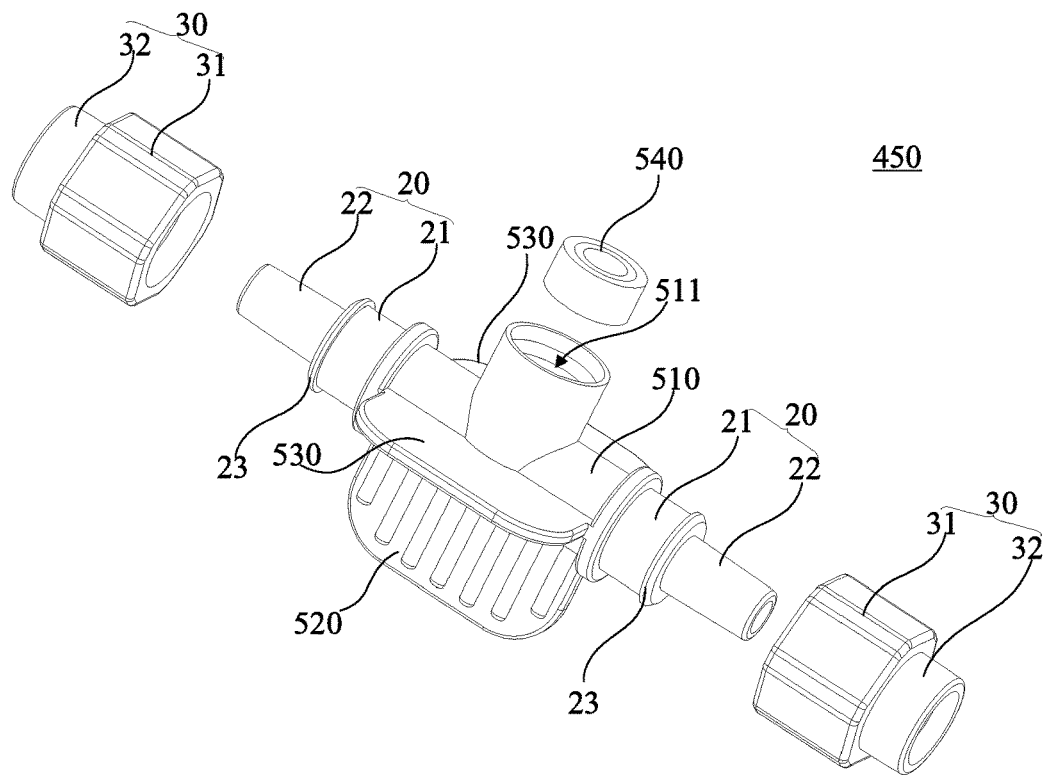
FIG. 24 is a schematic exploded view of a dosing joint in accordance with an embodiment.
Figure 25:
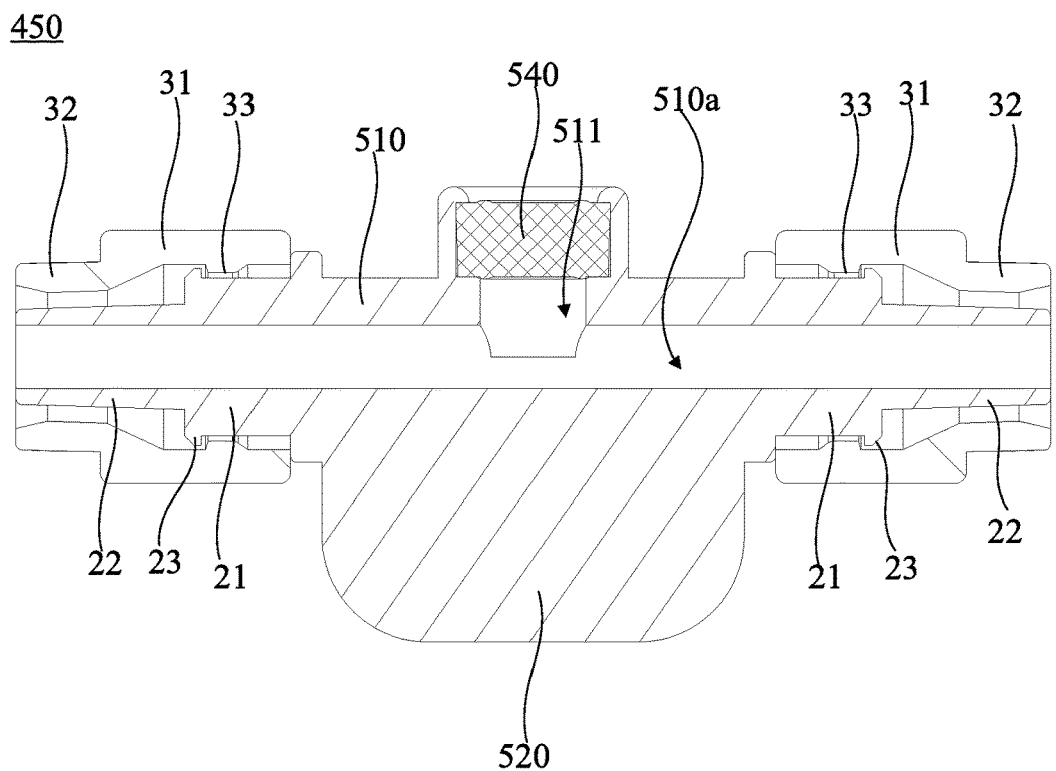
FIG. 25 is a sectional view of the dosing joint of FIG. 24 after assembly.

Referring to FIG. 7, FIG. 24, and FIG. 25, the circulation pipeline for hyperthermic perfusion 400 further includes a dosing joint 450, which is connected in series to the liquid inlet pipeline 101. Chemotherapy drugs and the like can be injected into the liquid inlet pipeline 101 through the dosing joint 450. The dosing joint 450 includes a dosing pipe body 510, a handle 520, and a protection flap 530. An infusion channel 510a in communication with the liquid inlet pipeline 101 is formed inside the dosing pipe body 510. A dosing hole 511 in communication with the infusion channel 510a is formed on a side wall of the dosing pipe body 510. The dosing pipe body 510 is provided with a dosing soft plug 540 for sealing the dosing hole 511 to prevent air or other dust from entering the pipeline system. Specifically, the dosing soft plug 540 may be a silicone plug. Certainly, in other embodiments, the dosing soft plug 540 may also be made of other soft materials, as long as the dosing soft plug 540 is capable of sealing the dosing hole 511 and being inserted by a needle tip of a syringe.

The handle 520 is disposed on an outer side wall of the dosing pipe body 510 and is spaced apart from the dosing hole 511. The protection flap 530 is disposed on the outer side wall of the dosing pipe body 510 and is located between the dosing hole 511 and the handle 520 to form a protection wall. Therefore, when one hand holds the handle 520 and the other hand holds the syringe and the needle tip of the syringe is inserted into the dosing soft plug 540, the protection flap 530 forms a protection wall between the hand and the needle tip, which may effectively prevent the needle tip from hurting the hands due to careless operation.

Figure 26:
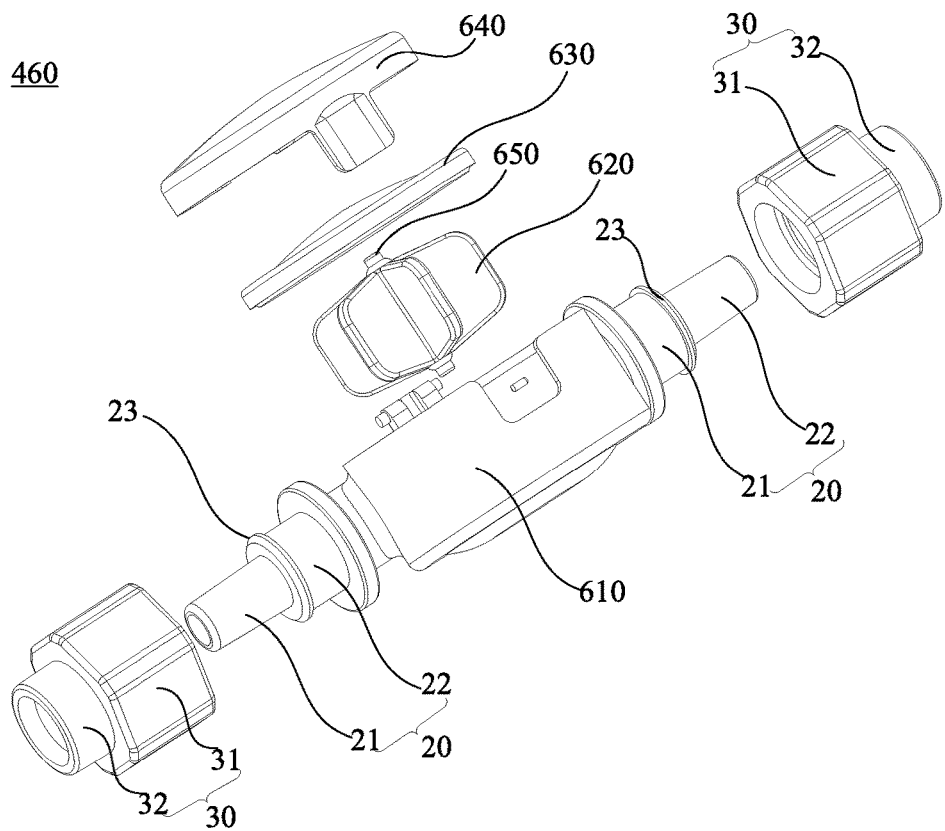
FIG. 26 is a schematic exploded view of a cavity inlet flow indicator in accordance with an embodiment.
Figure 27:
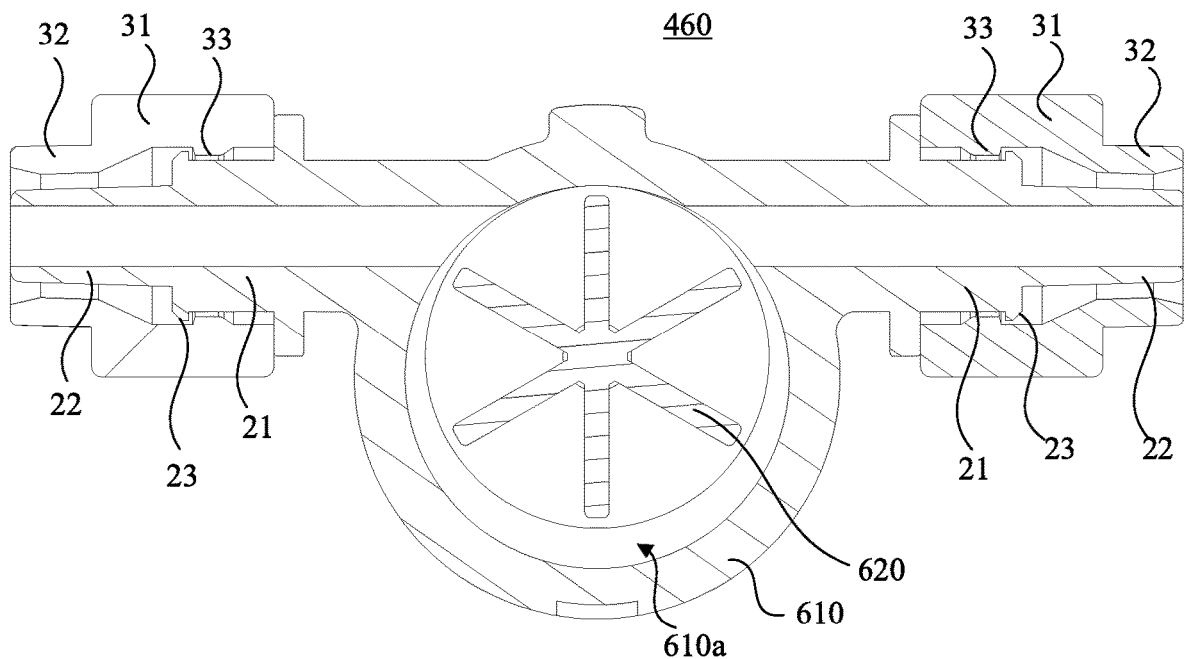
FIG. 27 is a sectional view of the cavity inlet flow indicator of FIG. 26 after assembly.

Referring to FIG. 7, FIG. 26, and FIG. 27, the circulation pipeline for hyperthermic perfusion 400 further includes a cavity inlet flow indicator 460, which is connected in series to the liquid outlet pipeline 102. For example, in the present embodiment, the cavity inlet flow indicator 460 is located behind the station of the pressure measuring assembly 430. The cavity inlet flow indicator 460 may be more beneficial for observing a flow status of the liquid in the pipeline system.

Specifically, the cavity inlet flow indicator 460 includes a seating 610, an impeller 620, a transparent cover body 630, and a light-shielding upper cover 640. The seating 610 is formed with an impeller cavity 610*a* that is in communication with the liquid outlet pipeline 102. The impeller 620 is rotatably disposed on the seating 610 through a rotating shaft 650 and is located in the impeller cavity 610*a*. The transparent cover body 630 is disposed on the seating 610 to seal the impeller cavity 610*a*. The light-shielding upper cover 640 is coverably disposed on the seating 610, and is capable of covering the transparent cover body 630.

The seating 610 is made of a light-shielding material, and the transparent cover body 630 may be made of a transparent material, such as transparent plastic or transparent glass. When the liquid enters the impeller cavity 610*a*, the impeller 620 is washed due to the continuity of the liquid. The impeller 620 may rotate under the action of the flowing liquid, and whether the liquid is in a flowing state can be known by observing whether the impeller 620 rotates through the transparent cover 630.

The impeller 620 is eccentrically disposed with respect to the impeller cavity 610*a* to accommodate a lower flow velocity. For example, in the case of that a flow indicator is applied to a bladder 10' circulation hyperthermic perfusion device, during the treatment, the flow velocity in the pipeline system is generally between 50 ml/min and 200 ml/min, in most cases, the flow velocity is lower than 150 ml/min. Such flow velocity is relatively low, thereby requiring increased sensitivity to rotation of the impeller 620.

Figure 28:
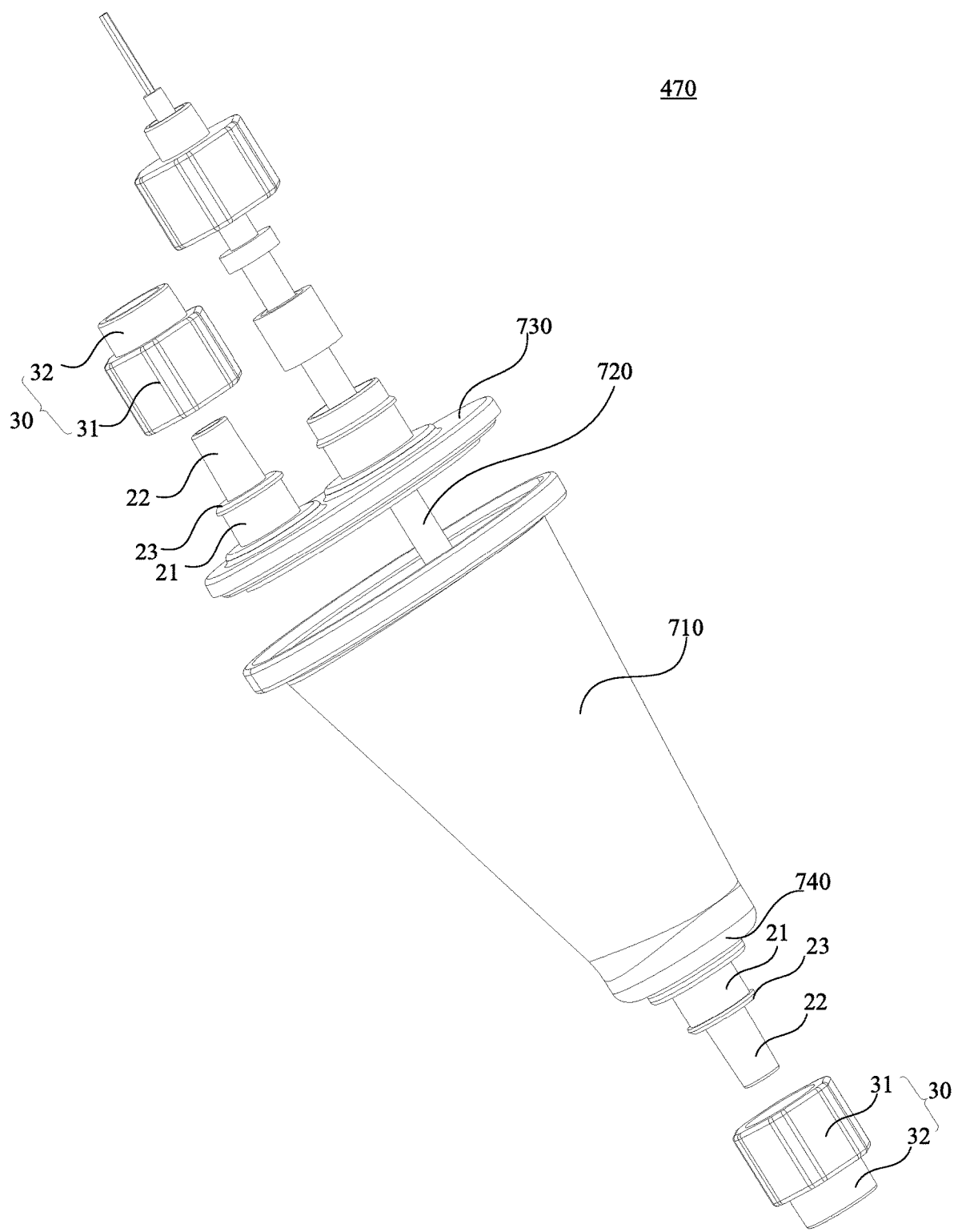
FIG. 28 is a schematic exploded view of a cavity inlet thermometer in accordance with an embodiment.
Figure 29:
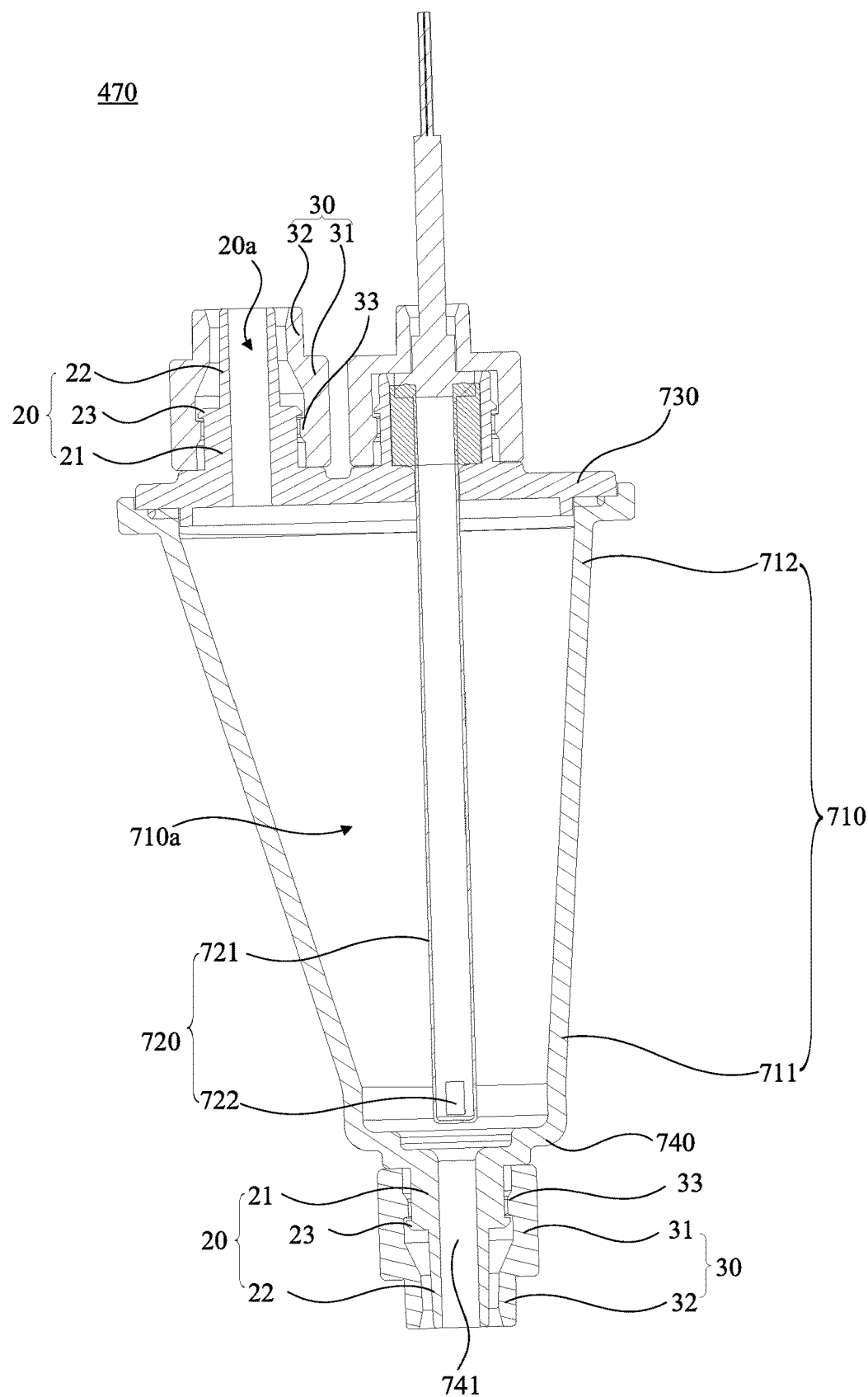
FIG. 29 is a sectional view of the cavity inlet thermometer of FIG. 28 after assembly.

Referring to FIG. 8 and FIG. 28 to FIG. 29, the circulation pipeline for hyperthermic perfusion 400 further includes a cavity inlet thermometer 470. The cavity inlet thermometer 470 is connected in series to the liquid outlet pipeline 102 and is configured to measure the temperature of the liquid flowing in the liquid outlet pipeline 102 in real time and truthfully, so as to monitor the true temperature of the liquid entering the bladder 10'. For example, in the present embodiment, the cavity inlet thermometer 470 is located behind the station of the cavity inlet flow indicator 460.

The cavity inlet thermometer 470 includes a first liquid storage housing 710, a second temperature measuring assembly 720, a first cavity inlet end cover 730, and a second cavity inlet end cover 740. An interior of the first liquid storage housing 710 is hollow to form a first liquid storage cavity 710*a* in communication with the liquid outlet pipeline 102. The first liquid storage housing 710 includes a first small-diameter end 711 and a first large-diameter end which are oppositely disposed. An inner diameter of the first small-diameter end 711 is less than an inner diameter of the first large-diameter end 712.

The second temperature measuring assembly 720 includes a second hollow pipe 721 and a second temperature sensor. The second temperature sensor has a second probe end 722 extending into the second hollow pipe 721 and located on an end of the second hollow pipe 721. The first cavity inlet end cover 730 covers the first large-diameter end 712 of the first liquid storage housing 710, and the second cavity inlet end cover 740 is disposed on the first small-diameter end 711 of the first liquid storage housing 710. The second hollow pipe 721 extends into the first liquid storage cavity 710*a* from the first cavity inlet end cover 730 and is adjacent to the first liquid inlet through hole 741 on the second cavity inlet end cover 740.

If the second probe end 722 of the second temperature sensor is too close to a side wall of the first liquid storage housing 710 or directly adheres to the side wall of the first liquid storage housing 710, the measured temperature will be 1° C. to 2° C. lower than the actual temperature of the liquid because of the inevitable heat dissipation of the first liquid storage housing 710. If the second probe end 722 of the second temperature sensor is located in the middle of the first liquid storage cavity 710*a*, since there is a dead water zone or the flow velocity less than the actual flow velocity of the liquid in the pipeline, the measured temperature will also be 1° C. lower than the actual temperature of the liquid. Therefore, in the present embodiment, the second probe end 722 is disposed adjacent to the first liquid inlet through hole, but is not in direct contact with the first liquid storage housing 710.

Referring to FIG. 8, the circulation pipeline for hyperthermic perfusion 400 further includes a cavity outlet thermometer 470', which is connected in series to the liquid return pipeline 104 and is configured to measure the temperature of the liquid flowing from the bladder 10' through the cavity outlet pipeline 106 in real time and truthfully. Specifically, the structure of the cavity outlet thermometer 470' is substantially the same as the structure of the cavity inlet thermometer 470.

The cavity outlet thermometer 470' includes a second liquid storage housing, a third temperature measuring assembly, a first cavity outlet end cover, and a second cavity outlet end cover. An interior of the second liquid storage housing is hollow to form a second liquid storage cavity in communication with the liquid return pipeline. The second liquid storage housing includes a second small-diameter end and a second large-diameter end which are oppositely disposed. An inner diameter of the second small-diameter end is less than an inner diameter of the second large-diameter end.

The third temperature measuring assembly includes a third hollow pipe and a third temperature sensor. The third temperature sensor has a third probe end extending into the third hollow pipe and located at an end of the third hollow pipe. The first cavity outlet end cover covers the second large-diameter end of the second liquid storage housing, and the second cavity outlet end cover is disposed on the second small-diameter end of the second liquid storage housing. The third hollow pipe extends into the second liquid storage cavity from the first cavity outlet end cover and is adjacent to the second liquid inlet through hole on the second cavity outlet end cover.

If the third probe end of the third temperature sensor is too close to the side wall of the second liquid storage housing or directly adheres to the side wall of the second liquid storage housing, the measured temperature will be 1° C. to 2° C. lower than the actual temperature of the liquid because of the inevitable heat dissipation of the second liquid storage housing. If the third probe end of the third temperature sensor is located in the middle of the second liquid storage cavity, since there is a dead water zone or the flow velocity less than the actual flow velocity of the liquid in the pipeline, the measured temperature will also be 1° C. lower than the actual temperature of the liquid. Therefore, in the present embodiment, the third probe end is disposed adjacent to the second liquid inlet through hole, but is not in direct contact with the second liquid storage housing.

Figure 30:
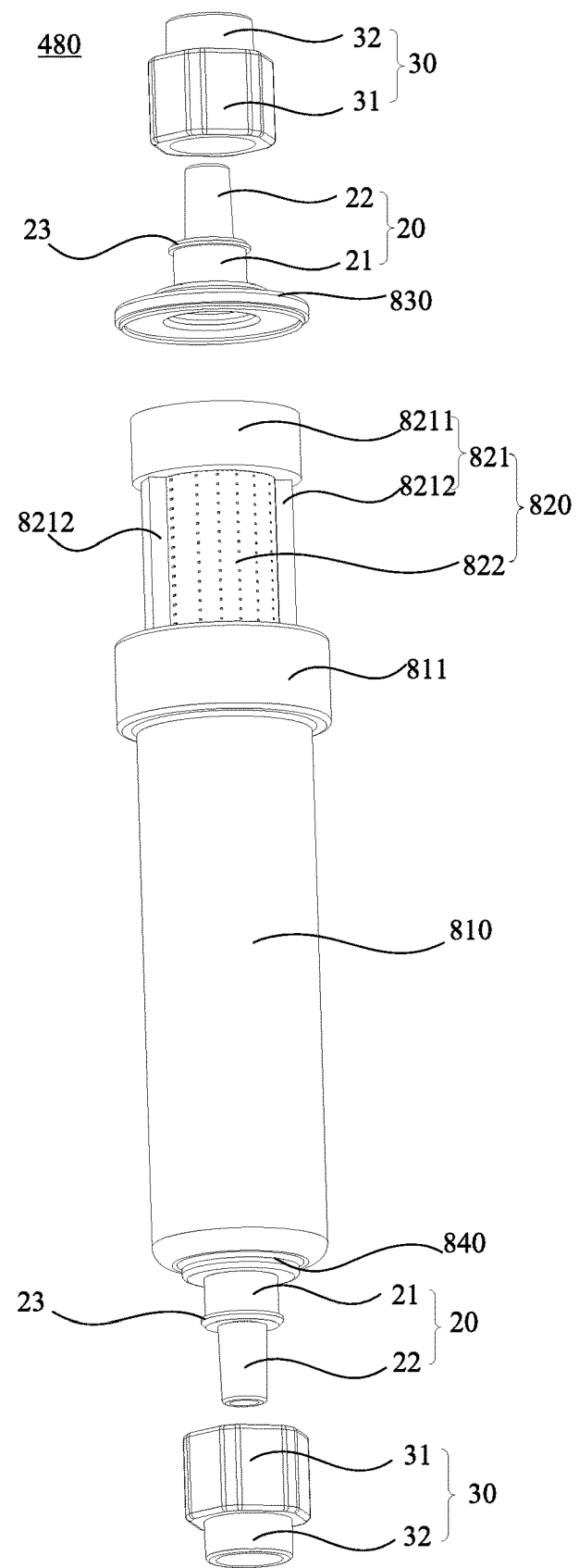
FIG. 30 is a schematic exploded view of a filter in accordance with an embodiment.
Figure 31:
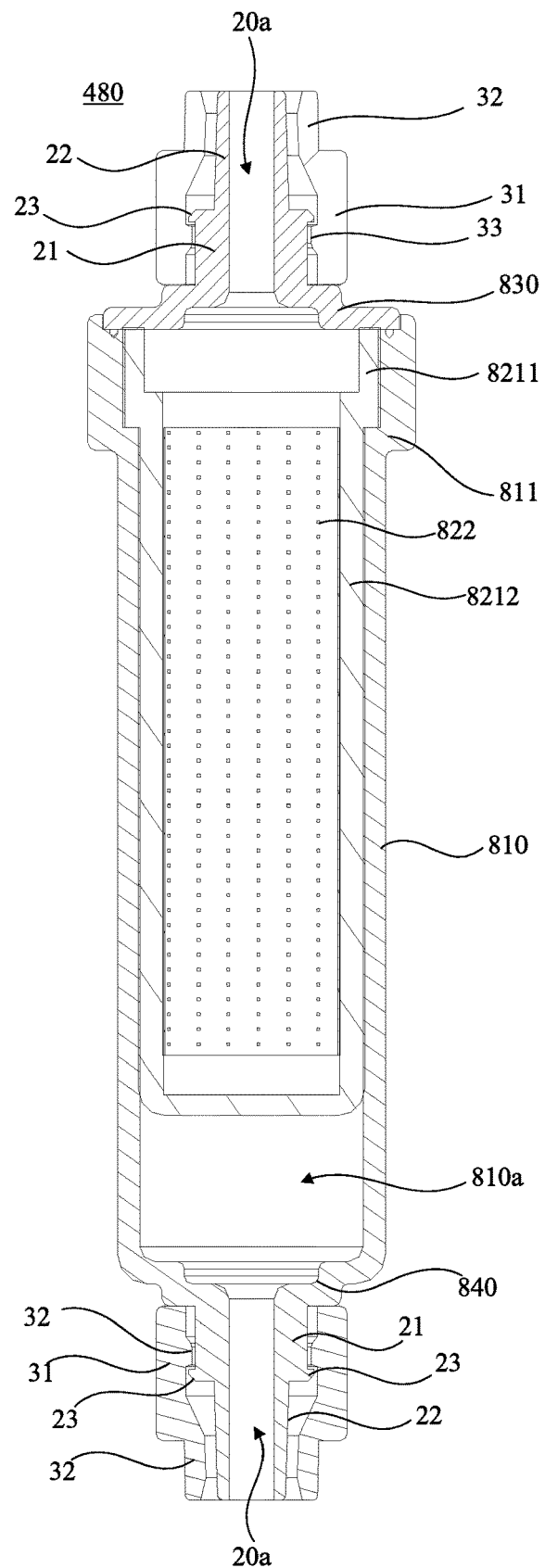
FIG. 31 is a sectional view of the filter of FIG. 30 after assembly.

Referring to FIG. 7, FIG. 30, and FIG. 31, the circulation pipeline for hyperthermic perfusion 400 further includes a filter 480 connected in series to the liquid return pipeline 104. For example, the filter 480 is located behind the station of the cavity outlet thermometer 470'. The filter 480 can filter the medicinal solution flowing out of the bladder 10' to prevent dropped tissues from damaging other components and parts.

Specifically, the filter 480 includes a housing 810, a filter element 820, an upper cover 830, and a lower cover 840. The housing 810 is formed with a filter element cavity 810a that is in communication with the liquid return pipeline 104. The filter element 820 is received in the filter element cavity 810a and is configured to filter the medicinal solution. Specifically, the housing 810 may be hollow cylindrical. The filter element 820 includes a holder 821 and a filter screen 822, and the filter screen 822 is disposed on the holder 821. The upper cover 830 is disposed on one end of the housing 810, and the lower cover 840 is disposed on the other end of the housing 810.

A side wall of one end of the housing 810 protrudes outward to form a positioning step 811. The holder 821 includes a positioning cylinder 8211 and at least two reinforcing ribs 8212. The positioning cylinder 8211 abuts against the positioning step 811. One end of each reinforcing rib 8212 is disposed on the positioning cylinder 8211. The reinforcing ribs 8212 are distributed at intervals in the radial direction. When the filter element 820 is assembled into the housing 810, one end of the filter element 820 extends into the filter element cavity 810a until the positioning cylinder 8211 abuts against the positioning step 811 to complete the assembly, so that the assembly and disassembly are facilitated.

Referring to FIG. 7, the circulation pipeline for hyperthermic perfusion 400 further includes a cavity outlet flow indicator 460' that is connected in series to the liquid return pipeline 104. For example, in the present embodiment, the cavity outlet flow indicator 460' is connected in series behind the station of the filter 480. The structure of the cavity outlet flow indicator 460' is substantially the same as the structure of the cavity inlet flow indicator 460.

Specifically, the cavity outlet flow indicator 460' includes a seating 610, an impeller 620, a transparent cover body 630, and a light-shielding upper cover 640. The seating 610 is formed with an impeller cavity 610a in communication with the liquid outlet pipeline 104. The impeller 620 is rotatably disposed on the seating 610 through a rotating shaft and is located within the impeller cavity 610a. The transparent cover body 630 is disposed on the seating 610 to seal the impeller cavity 610a. The light-shielding upper cover 640 is coverably disposed on the seating 610 and is capable of covering the transparent cover body 630.

The seating 610 is made of a light-shielding material, and the transparent cover body 630 may be made of a transparent material, such as transparent plastic or transparent glass. When the liquid enters the impeller cavity 610a, the impeller 620 is washed due to the continuity of the liquid. The impeller 620 may rotate under the action of the flowing liquid, and whether the liquid is in a flowing state can be known by observing whether the impeller 620 rotates through the transparent cover 630.

The impeller 620 is eccentrically disposed with respect to the impeller cavity 610a to accommodate a lower flow velocity. For example, in the case of that a flow indicator is applied to a bladder 10' circulation hyperthermic perfusion device, during the treatment, the flow velocity in the pipeline system is generally between 50 ml/min and 200 ml/min, in most cases, the flow velocity is lower than 150 ml/min. Such flow velocity is relatively low, thereby requiring increased sensitivity to rotation of the impeller 620.

Referring to FIG. 7, the circulation pipeline for hyperthermic perfusion 400 further includes a flow regulating valve 490, which is connected in series to the liquid return pipeline 104. For example, in the present embodiment, the flow regulating valve 490 is located behind the station of the cavity outlet flow indicator 460', and is configured to regulate a flow velocity of the medicinal solution in the liquid return pipeline 104.

Specifically, the liquid inlet pipeline 101, the liquid outlet pipeline 102, the pre-filling pipeline 103, the cavity inlet pipeline 105, the cavity outlet pipeline 106, and the liquid return pipeline 104 can all be flexible pipes made of soft materials. The flexible pipe may also have light-shielding properties to meet the requirements of that certain drugs for bladder 10' chemotherapy need to be shielded from light.

The two-way valve 440, the dosing joint 450, the pressure measuring assembly 430, the cavity inlet flow indicator 460, the cavity inlet thermometer 470, the cavity outlet thermometer 470', the filter 480, the cavity outlet flow indicator 460' and the flow regulating valve 490 can be connected in series to the pipeline system through a pure physical connection method in which the joint 20 and a locking sleeve 30 are matched, which may prevent the residue of an adhesive.

Specifically, a channel 20a is formed on the joint 20, and the liquid is in communication with the pipeline system through the channel 20a. The joint 20 includes a matching section 21 and a connecting section 22. A first protrusion 23 is formed on an outer side wall of the matching section 21. An outer side wall of the connecting section 22 is a conical surface. The locking sleeve 30 includes a first locking section 31 and a second locking section 32. A second protrusion 33 matched with the first protrusion 23 is formed on an inner side wall of the first locking section 31. An inner side wall of the second locking section 32 protrudes to form a pressing portion. The flexible pipe is compressed between the pressing portion and the connecting section 22.

When the locking sleeve 30 is matched with the joint, the locking sleeve 30 is sleeved into the flexible pipes in advance, and then one end of the flexible pipe is sleeved on the connecting section 22 of the joint. The flexible pipe is stretched by the connecting section 22 when being sleeved on the connecting section 22. The locking sleeve 30 is moved until the second protrusion 33 on the inner side wall of the first locking sleeve 30 passes through the first protrusion 23 on the outer side wall of the matching section 21, and the pressing portion of the inner side wall of the second locking section 32 has a certain pressing effect on the flexible pipe, so that the flexible pipe can be compressed between the connecting section 22 and the second locking section 32, which may prevent the flexible pipe from detaching from the joint.

Specifically, in the present embodiment, the device of intracavitary circulatory hyperthermic perfusion 10 further includes an intracavitary pressure measuring sensor 700, which is used to measure a pressure value in the bladder 10'.

Specifically, in the present embodiment, the controller includes a main control unit, a data acquisition unit, a power control unit, and a driving control unit. The data acquisition unit, the power control unit, and the driving control unit are electrically coupled to the main control unit. The touch display 500 is also electrically coupled to the main control unit. The weight data measured by the weighing sensor are transmitted to the data acquisition unit, and the data acquisition unit transmits weight data signals to the main control unit, which controls the electromagnetic induction coil to be powered on or powered off. The heating power of the electromagnetic induction coil is controlled by the power control unit to ensure that the treatment temperature is maintained at about 45° C. for a long time. The driving control unit is configured to control the first driving source and the second driving source. The first driving source drives the lifting platform to perform the lifting movement, and the second driving source drives the valve core to rotate relative to the valve body to achieve the purpose of opening and closing of the two-way valve.

The main control unit also obtains the temperature values of the medicinal solution measured by the first temperature sensor, the second temperature sensor, and the third temperature sensor in real time through the data acquisition unit, thereby obtaining the temperature values of the medicinal solution in the heating tank, the liquid outlet pipeline, and the liquid return pipeline. The touch display 500 can display the temperature values of the medicinal solution in the heating tank, the liquid outlet pipeline, and the liquid return pipeline. The main control unit also obtains the pressure value in the bladder 10' measured by the intracavitary pressure measuring sensor 700 through the data acquisition unit. The touch display 500 can display the pressure value, so that the pressure value in the heating tank can be adjusted by adjusting the sealing cap on the heating tank, which ensures that the temperature and the pressure in the bladder 10' are in a completely effective state. Thus, the effective killing effect of thermotherapy and chemotherapy on superficial bladder cancer can be better exerted.

Meanwhile, the total amount of the medicinal solution entering the bladder 10' calculated by the weighing sensor in real time is acquired by the data acquisition unit, and the pressure value in the bladder 10' monitored by the intracavitary pressure measuring sensor is acquired by the data acquisition unit. Based on this, the rotate speed of the roller pump is adjusted automatically, thereby adjusting the speed and the total amount of the medicinal solution entering the bladder 10', and ensuring that the pressure in the bladder 10' is within a safety threshold. When the relevant parameters such as the treatment temperature, the pressure and the like exceed the threshold value, automatic alarm protection is carried out.

The above-mentioned device of intracavitary circulatory hyperthermic perfusion 10 has at least the following advantages.

In use, the contact pin 108 is inserted into the medicinal solution bag, and the controller controls the driving mechanism 442 to drive the valve core 4411 of the two-way valve 440 to rotate relative to the valve body 4412, so that the two-way valve 440 is in an open state. The medicinal solution in the medicinal solution bag enters the liquid storage cavity 410a of the heating tank 410 through the liquid inlet pipeline 101, and the chemotherapeutic drug and the like can be injected into the liquid inlet pipeline 101 through the dosing joint 450. Since the heating tank 410 is the non-deformable tank structure, the sealing cap needs to be opened at this time, otherwise, the medicinal solution cannot be injected into the heating tank 410 due to an airtightness of the pipeline. The heating tank 410 is carried on a tray. When the weighing sensor detects that the amount of the medicinal solution in the heating tank 410 reaches a set value, the controller controls the driving mechanism 442 again to drive the valve core 4411 to rotate relative to the valve body 4412, so that the two-way valve 440 is closed, and the liquid inlet pipeline 101 is in a closed state. The medicinal solution in the heating tank 410 is preheated by the electromagnetic induction heating device until a preheating temperature is reached.

When the pipeline system needs to be pre-filled, the driving control unit drives the circulation pump 420 to drive the medicinal solution to flow. At this time, the pre-filling valve 1031 is opened, and the cavity inlet valve 1051 and the cavity outlet valve 1061 are closed. The medicinal solution is extracted out of the liquid storage cavity 410a under the action of the circulation pump 420. The pressure measuring assembly 430 is externally connected to the pressure measuring sensor and measures the pressure of the liquid in the liquid outlet pipeline 102. The medicinal solution passes through the cavity inlet flow indicator 460 and cavity inlet thermometer 470 in the liquid outlet pipeline 102, then is introduced into the pre-filling pipeline 103, and then flows back to the heating tank 410 through the cavity outlet thermometer 470', the filter 480, the cavity outlet flow indicator 460', and the flow regulating valve 490 in the liquid return pipeline 104. The medicinal solution flows back to the heating tank 410 through the liquid outlet pipeline 102, the pre-filling pipeline 103, and the liquid return pipeline 104, so that the air in the pipeline system can be exhausted in advance to avoid causing inflammation.

Then, the pre-filling valve 1031 is closed, the cavity inlet valve 1051 and the cavity outlet valve 1061 are opened. The medicinal solution is extracted out of the liquid storage cavity 410a again under the action of the circulation pump 420, and then enters the bladder 10' through the liquid outlet pipeline 102 and the cavity inlet pipeline 105. The pressure in the bladder 10' increases along with the increase of the medicinal solution in the bladder 10'. At this time, the medicinal solution flows back to the heating tank 410 through the cavity outlet pipeline 106 and the liquid return pipeline 104 under the action of the pressure difference and gravity of the bladder 10' itself, thereby forming a continuous circulation of the medicinal solution.

During the circulation process of the medicinal solution, the heating tank 410 can continuously heat the medicinal solution until the set temperature is reached, which achieves the purpose of simultaneous circulating and heating, thereby preventing the temperature of the medicinal solution from being rapidly heated at the beginning and avoiding the contraction or spasm of the bladder 10'. Since the medicinal solution is heated to the predetermined temperature before being introduced into the bladder 10' for treatment, after the medicinal solution is introduced into the bladder 10', a thermal killing mechanism can be fully exerted, metastatic cancer cells that are widely planted on serosa are killed, and the lesions that cause the malignant effusion can be eliminated, so that the purpose of effectively treating the cancerous effusion is achieved, and the treatment effect is effectively improved.

The above-mentioned embodiments only express several implementation manners of the present disclosure, and their descriptions are more specific and detailed, but they cannot be understood as limiting the scope of the invention disclosure. It should be noted that, for those of ordinary skill in the art, without departing from the concept of the present disclosure, several modifications and improvements can be made, which all belong to the protection scope of the present disclosure. Therefore, the protection scope of the invention disclosure shall be subject to the appended claims.

What is claimed is:

1. A device of intracavitary circulatory hyperthermic perfusion, comprising:
   a housing;
   an electromagnetic induction heating device disposed on the housing, the electromagnetic induction heating device comprising a tray and an electromagnetic induction coil, the electromagnetic induction coil being disposed on one side of the tray and configured to heat a heating tank capable of being carried on the tray;
   a controller comprising a main control unit, a data acquisition unit, and a power control unit, wherein the data acquisition unit and the power control unit are electrically coupled to the main control unit, the data acquisition unit is configured to acquire temperature values of a medicinal solution in the heating tank, a liquid outlet pipeline, and a liquid return pipeline and to transmit the temperature values to the main control unit, and the main control unit controls the power control unit according to the temperature values of the medicinal solution to control a heating power of the electromagnetic induction coil; and
   a lifting mechanism comprising a lifting assembly and a lifting platform, the lifting assembly is disposed on the housing and comprises a first driving source, a driving shaft, and a lifting block, the first driving source is capable of driving the lifting block to move reciprocally along a lifting direction through the driving shaft, the lifting platform is fixed on the lifting block and moves along with a movement of the lifting block, and the tray is disposed on the lifting platform.

2. The device of intracavitary circulatory hyperthermic perfusion of claim 1, further comprising a dustproof assembly, wherein the dustproof assembly comprises a lifting seat, a dustproof belt, an upper rolling shaft, and a lower rolling shaft, the lifting assembly is located inside the housing, the lifting platform is fixed on the lifting block through the lifting seat and moves along with the movement of the lifting block, the upper rolling shaft and the lower rolling shaft are both rotatably disposed inside the housing, one end of the dustproof belt is fixed on the lifting seat, another end of the dustproof belt is fixed on the lifting seat after passing around the upper rolling shaft, passing through the lifting seat, and passing around the lower rolling shaft, the lifting seat is provided with a mounting portion exposed to the housing through a sliding groove on the housing, and the dustproof belt abuts against an inner side wall of the housing to shield the sliding groove.

3. The device of intracavitary circulatory hyperthermic perfusion of claim 1, wherein the electromagnetic induction heating device further comprises a weighing sensor, the weighing sensor is disposed below the tray and is configured to measure a weight of the medicinal solution in the heating tank carried on the tray, the weighing sensor controls the electromagnetic induction coil to be powered on or off through the controller.

4. The device of intracavitary circulatory hyperthermic perfusion of claim 3, further comprising a touch display, wherein the touch display is disposed on the housing and is electrically coupled to the controller, and the weighing sensor and the electromagnetic induction coil are electrically coupled to the controller.

5. The device of intracavitary circulatory hyperthermic perfusion of claim 1, further comprising a circulation pipeline for hyperthermic perfusion, wherein the circulation pipeline for hyperthermic perfusion comprises the heating, a liquid inlet pipeline, the liquid outlet pipeline, a circulation pump, a cavity inlet pipeline, and a cavity outlet pipeline, the heating tank is hollow to form a liquid storage cavity configured to store the medicinal solution, the heating tank is carried on the tray, the electromagnetic induction coil is configured to heat the heating tank to indirectly heat the medicinal solution stored in the liquid storage cavity, one end of the liquid inlet pipeline is in communication with the liquid storage cavity, and another end of the liquid inlet pipeline is configured to be in communication with a medicinal solution bag, one end of the liquid outlet pipeline is in communication with the liquid storage cavity, and another end of the liquid outlet pipeline is in communication with one end of the cavity inlet pipeline, another end of the cavity inlet pipeline is configured to be in communication with a body cavity, one end of the cavity outlet pipeline is configured to be in communication with the body cavity, and another end of the cavity outlet pipeline is in communication with one end of the liquid return pipeline, and another end of the liquid return pipeline is in communication with the liquid storage cavity.

6. The device of intracavitary circulatory hyperthermic perfusion of claim 5, wherein the heating tank comprises a tank body and a cover body, the tank body is hollow, and one end of the tank body is opened to form an open end, the cover body is disposed on the open end of the tank body, the cover body and the tank body together form the liquid storage cavity;
   wherein the tank body comprises a tank shell and a base, the base is disposed on a bottom of the tank shell, the tank shell is made of plastic materials, and the base is made of metal materials, and the base and the tank shell are integrally formed by an injection molding; or
   the tank body is integrally made of metal materials; or
   the tank body has a bottom away from the open end, and the bottom of the tank body is made of metal materials.

7. The device of intracavitary circulatory hyperthermic perfusion of claim 6, wherein the heating tank further comprises an air filter and a sealing cap, a matching joint is formed on the cover body, the air filter is in communication with the liquid storage cavity through the matching joint, and the sealing cap is capable of sealing the air filter.

8. The device of intracavitary circulatory hyperthermic perfusion of claim 6, wherein the heating tank further comprises a first temperature measuring assembly comprising a first temperature sensor and a first hollow pipe, the first temperature sensor has a first probe end extending into the first hollow pipe and located on an end of the first hollow pipe, and one end of the first hollow pipe extends into the liquid storage cavity and is disposed proximate to a bottom of the tank body.

9. The device of intracavitary circulatory hyperthermic perfusion of claim 6, wherein the circulation pipeline for hyperthermic perfusion further comprises one or more of the following:
   a pressure measuring assembly connected in series to the liquid outlet pipeline and located behind a station of the circulation pump, wherein the pressure measuring assembly is configured to measure a pressure in the liquid outlet pipeline behind the station of the circulation pump;
   a two-way valve connected in series to the liquid inlet pipeline, wherein the two-way valve is configured to control opening and closing of the liquid inlet pipeline, the two-way valve comprises a valve main body comprising a valve core and a valve body, the valve core is provided with a liquid through hole, at least one end of the valve body is opened and an interior of the valve body is hollow to form a receiving cavity, a first liquid inlet channel and a first liquid outlet channel which are in communication with the receiving cavity are formed on a side wall of the valve body, one end of the valve core extends into the receiving cavity, and the valve core is rotatable relative to the valve body, so that the liquid through hole is capable of being or being not in communication with the first liquid inlet channel and the first liquid outlet channel;

a dosing joint connected in series to the liquid inlet pipeline, wherein the dosing joint comprises a dosing pipe body, a handle, and a protection flap, an infusion channel in communication with the liquid inlet pipeline is formed inside the dosing pipe body, a dosing hole in communication with the infusion channel is formed on a side wall of the dosing pipe body, the dosing pipe body is provided with a dosing soft plug configured to seal the dosing hole, the handle is disposed on an outer side wall of the dosing pipe body and is spaced apart from the dosing hole, and the protection flap is disposed on the outer side wall of the dosing pipe body and is located between the dosing hole and the handle to form a protection wall;

a cavity inlet flow indicator connected in series to the liquid outlet pipeline, wherein the cavity inlet flow indicator comprises a seating, an impeller, a transparent cover body, and a light-shielding upper cover, the seating is formed with an impeller cavity in communication with the liquid outlet pipeline, the impeller is rotatably disposed on the seating through a rotating shaft and is located within the impeller cavity, the transparent cover body is disposed on the seating to seal the impeller cavity, and the light-shielding upper cover is coverably disposed on the seating and is capable of covering the transparent cover body;

a cavity inlet thermometer connected in series to the liquid outlet pipeline, wherein the cavity inlet thermometer comprises a first liquid storage housing, a second temperature measuring assembly, a first cavity inlet end cover, and a second cavity inlet end cover, an interior of the first liquid storage housing is hollow to form a first liquid storage cavity in communication with the liquid outlet pipeline, the first liquid storage housing comprises a first small-diameter end and a first large-diameter end which are oppositely disposed, an inner diameter of the first small-diameter end is less than an inner diameter of the first large-diameter end, the second temperature measuring assembly comprises a second hollow pipe and a second temperature sensor, the second temperature sensor has a second probe end extending into the second hollow pipe and located on an end of the second hollow pipe, the first cavity inlet end cover covers the first large-diameter end of the first liquid storage housing, and the second cavity inlet end cover is disposed on the first small-diameter end of the first liquid storage housing, the second hollow pipe extends into the first liquid storage cavity from the first cavity inlet end cover and is adjacent to a first liquid inlet through hole on the second cavity inlet end cover;

a cavity outlet thermometer connected in series to the liquid return pipeline, wherein the cavity outlet thermometer comprises a second liquid storage housing, a third temperature measuring assembly, a first cavity outlet end cover, and a second cavity outlet end cover, an interior of the second liquid storage housing is hollow to form a second liquid storage cavity in communication with the liquid return pipeline, the second liquid storage housing comprises a second small-diameter end and a second large-diameter end which are oppositely disposed, an inner diameter of the second small-diameter end is less than an inner diameter of the second large-diameter end, the third temperature measuring assembly comprises a third hollow pipe and a third temperature sensor, the third temperature sensor has a third probe end extending into the third hollow pipe and located on an end of the third hollow pipe, the first cavity outlet end cover covers the second large-diameter end of the second liquid storage housing, the second cavity outlet end cover is disposed on the second small-diameter end of the second liquid storage housing, and the third hollow pipe extends into the second liquid storage cavity from the first cavity outlet end cover and is adjacent to a second liquid inlet through hole on the second cavity outlet end cover;

a filter connected in series to the liquid return pipeline, wherein the filter comprises a housing, a filter element, an upper cover, and a lower cover, the housing is formed with a filter element cavity in communication with the liquid return pipeline, the filter element is received in the filter element cavity and is configured to filter the medicinal solution, the upper cover is disposed on one end of the housing, and the lower cover is disposed on another end of the housing;

a cavity outlet flow indicator connected in series to the liquid return pipeline, wherein the cavity outlet flow indicator comprises a seating, an impeller, a transparent cover body, and a light-shielding upper cover, the seating is formed with an impeller cavity in communication with the liquid outlet pipeline, the impeller is rotatably disposed on the seating through a rotating shaft and is located within the impeller cavity, the transparent cover body is disposed on the seating to seal the impeller cavity, and the light-shielding upper cover is coverably disposed on the seating and is capable of covering the transparent cover body; and a flow regulating valve connected in series to the liquid return pipeline, wherein the flow regulating valve is configured to regulate a flow velocity of the medicinal solution in the liquid return pipeline.

10. A device of intracavitary circulatory hyperthermic perfusion, comprising:

a housing;

an electromagnetic induction heating device disposed on the housing, the electromagnetic induction heating device comprising a tray and an electromagnetic induction coil, the electromagnetic induction coil being disposed on one side of the tray and configured to heat a heating tank capable of being carried on the tray;

a controller comprising a main control unit, a data acquisition unit, and a power control unit, wherein the data acquisition unit and the power control unit are electrically coupled to the main control unit, the data acquisition unit is configured to acquire temperature values of a medicinal solution in the heating tank, a liquid outlet pipeline, and a liquid return pipeline and to transmit the temperature values to the main control unit, and the main control unit controls the power control unit according to the temperature values of the medicinal solution to control a heating power of the electromagnetic induction coil; and wherein the electromagnetic induction heating device further comprises a weighing sensor, the weighing sensor is disposed below the tray and is configured to measure a weight of the medicinal solution in the heating tank carried on the tray, the weighing sensor controls the electromagnetic induction coil to be powered on or off through the controller.

11. The device of intracavitary circulatory hyperthermic perfusion of claim 10, further comprising a touch display, wherein the touch display is disposed on the housing and is electrically coupled to the controller, and the weighing sensor and the electromagnetic induction coil are electrically coupled to the controller.

12. The device of intracavitary circulatory hyperthermic perfusion of claim 10, further comprising a circulation pipeline for hyperthermic perfusion, wherein the circulation pipeline for hyperthermic perfusion comprises the heating tank, a liquid inlet pipeline, the liquid outlet pipeline, a circulation pump, a cavity inlet pipeline, and a cavity outlet pipeline, the heating tank is hollow to form a liquid storage cavity configured to store the medicinal solution, the heating tank is carried on the tray, the electromagnetic induction coil is configured to heat the heating tank to indirectly heat the medicinal solution stored in the liquid storage cavity, one end of the liquid inlet pipeline is in communication with the liquid storage cavity, and another end of the liquid inlet pipeline is configured to be in communication with a medicinal solution bag, one end of the liquid outlet pipeline is in communication with the liquid storage cavity, and another end of the liquid outlet pipeline is in communication with one end of the cavity inlet pipeline, another end of the cavity inlet pipeline is configured to be in communication with a body cavity, one end of the cavity outlet pipeline is configured to be in communication with the body cavity, and another end of the cavity outlet pipeline is in communication with one end of the liquid return pipeline, and another end of the liquid return pipeline is in communication with the liquid storage cavity.

13. The device of intracavitary circulatory hyperthermic perfusion of claim 12, wherein the heating tank comprises a tank body and a cover body, the tank body is hollow, and one end of the tank body is opened to form an open end, the cover body is disposed on the open end of the tank body, the cover body and the tank body together form a liquid storage cavity;
wherein the tank body comprises a tank shell and a base, the base is disposed on a bottom of the tank shell, the tank shell is made of plastic materials, and the base is made of metal materials, and the base and the tank shell are integrally formed by an injection molding; or
the tank body is integrally made of metal materials; or
the tank body has a bottom away from the open end, and the bottom of the tank body is made of metal materials.

14. The device of intracavitary circulatory hyperthermic perfusion of claim 13, wherein the heating tank further comprises an air filter and a sealing cap, a matching joint is formed on the cover body, the air filter is in communication with the liquid storage cavity through the matching joint, and the sealing cap is capable of sealing the air filter.

15. The device of intracavitary circulatory hyperthermic perfusion of claim 13, wherein the heating tank further comprises a first temperature measuring assembly comprising a first temperature sensor and a first hollow pipe, the first temperature sensor has a first probe end extending into the first hollow pipe and located on an end of the first hollow pipe, and one end of the first hollow pipe extends into the liquid storage cavity and is disposed proximate to the bottom of the tank body.

16. The device of intracavitary circulatory hyperthermic perfusion of claim 2, wherein the circulation pipeline for hyperthermic perfusion further comprises one or more of the following:
a pressure measuring assembly connected in series to the liquid outlet pipeline and located behind a station of the circulation pump, wherein the pressure measuring assembly is configured to measure a pressure in the liquid outlet pipeline behind the station of the circulation pump;
a two-way valve connected in series to the liquid inlet pipeline, wherein the two-way valve is configured to control opening and closing of the liquid inlet pipeline, the two-way valve comprises a valve main body comprising a valve core and a valve body, the valve core is provided with a liquid through hole, at least one end of the valve body is opened and an interior of the valve body is hollow to form a receiving cavity, a first liquid inlet channel and a first liquid outlet channel which are in communication with the receiving cavity are formed on a side wall of the valve body, one end of the valve core extends into the receiving cavity, and the valve core is rotatable relative to the valve body, so that the liquid through hole is capable of being or being not in communication with the first liquid inlet channel and the first liquid outlet channel;
a dosing joint connected in series to the liquid inlet pipeline, wherein the dosing joint comprises a dosing pipe body, a handle, and a protection flap, an infusion channel in communication with the liquid inlet pipeline is formed inside the dosing pipe body, a dosing hole in communication with the infusion channel is formed on a side wall of the dosing pipe body, the dosing pipe body is provided with a dosing soft plug configured to seal the dosing hole, the handle is disposed on an outer side wall of the dosing pipe body and is spaced apart from the dosing hole, and the protection flap is disposed on the outer side wall of the dosing pipe body and is located between the dosing hole and the handle to form a protection wall;
a cavity inlet flow indicator connected in series to the liquid outlet pipeline, wherein the cavity inlet flow indicator comprises a seating, an impeller, a transparent cover body, and a light-shielding upper cover, the seating is formed with an impeller cavity in communication with the liquid outlet pipeline, the impeller is rotatably disposed on the seating through a rotating shaft and is located within the impeller cavity, the transparent cover body is disposed on the seating to seal the impeller cavity, and the light-shielding upper cover is coverably disposed on the seating and is capable of covering the transparent cover body;
a cavity inlet thermometer connected in series to the liquid outlet pipeline, wherein the cavity inlet thermometer comprises a first liquid storage housing, a second temperature measuring assembly, a first cavity inlet end cover, and a second cavity inlet end cover, an interior of the first liquid storage housing is hollow to form a first liquid storage cavity in communication with the liquid outlet pipeline, the first liquid storage housing comprises a first small-diameter end and a first large-diameter end which are oppositely disposed, an inner diameter of the first small-diameter end is less than an inner diameter of the first large-diameter end, the second temperature measuring assembly comprises a second hollow pipe and a second temperature sensor, the second temperature sensor has a second probe end extending into the second hollow pipe and located on an end of the second hollow pipe, the first cavity inlet end cover covers the first large-diameter end of the first liquid storage housing, and the second cavity inlet end cover is disposed on the first small-diameter end of the first liquid storage housing, the second hollow pipe extends into the first liquid storage cavity from the first cavity inlet end cover and is adjacent to a first liquid inlet through hole on the second cavity inlet end cover;

a cavity outlet thermometer connected in series to the liquid return pipeline, wherein the cavity outlet thermometer comprises a second liquid storage housing, a third temperature measuring assembly, a first cavity outlet end cover, and a second cavity outlet end cover, an interior of the second liquid storage housing is hollow to form a second liquid storage cavity in communication with the liquid return pipeline, the second liquid storage housing comprises a second small-diameter end and a second large-diameter end which are oppositely disposed, an inner diameter of the second small-diameter end is less than an inner diameter of the second large-diameter end, the third temperature measuring assembly comprises a third hollow pipe and a third temperature sensor, the third temperature sensor has a third probe end extending into the third hollow pipe and located on an end of the third hollow pipe, the first cavity outlet end cover covers the second large-diameter end of the second liquid storage housing, the second cavity outlet end cover is disposed on the second small-diameter end of the second liquid storage housing, and the third hollow pipe extends into the second liquid storage cavity from the first cavity outlet end cover and is adjacent to a second liquid inlet through hole on the second cavity outlet end cover;

a filter connected in series to the liquid return pipeline, wherein the filter comprises a housing, a filter element, an upper cover, and a lower cover, the housing is formed with a filter element cavity in communication with the liquid return pipeline, the filter element is received in the filter element cavity and is configured to filter the medicinal solution, the upper cover is disposed on one end of the housing, and the lower cover is disposed on another end of the housing;

a cavity outlet flow indicator connected in series to the liquid return pipeline, wherein the cavity outlet flow indicator comprises a seating, an impeller, a transparent cover body, and a light-shielding upper cover, the seating is formed with an impeller cavity in communication with the liquid outlet pipeline, the impeller is rotatably disposed on the seating through a rotating shaft and is located within the impeller cavity, the transparent cover body is disposed on the seating to seal the impeller cavity, and the light-shielding upper cover is coverably disposed on the seating and is capable of covering the transparent cover body; and a flow regulating valve connected in series to the liquid return pipeline, wherein the flow regulating valve is configured to regulate a flow velocity of the medicinal solution in the liquid return pipeline.

17. A device of intracavitary circulatory hyperthermic perfusion, comprising:
a housing;
an electromagnetic induction heating device disposed on the housing, the electromagnetic induction heating device comprising a tray and an electromagnetic induction coil, the electromagnetic induction coil being disposed on one side of the tray and configured to heat a heating tank capable of being carried on the tray;
a controller comprising a main control unit, a data acquisition unit, and a power control unit, wherein the data acquisition unit and the power control unit are electrically coupled to the main control unit, the data acquisition unit is configured to acquire temperature values of a medicinal solution in the heating tank, a liquid outlet pipeline, and a liquid return pipeline and to transmit the temperature values to the main control unit, and the main control unit controls the power control unit according to the temperature values of the medicinal solution to control a heating power of the electromagnetic induction coil; and
a circulation pipeline for hyperthermic perfusion, wherein the circulation pipeline for hyperthermic perfusion comprises the heating tank, a liquid inlet pipeline, the liquid outlet pipeline, a circulation pump, a cavity inlet pipeline, and a cavity outlet pipeline, the heating tank is hollow to form a liquid storage cavity configured to store the medicinal solution, the heating tank is carried on the tray, the electromagnetic induction coil is configured to heat the heating tank to indirectly heat the medicinal solution stored in the liquid storage cavity, one end of the liquid inlet pipeline is in communication with the liquid storage cavity, and another end of the liquid inlet pipeline is configured to be in communication with a medicinal solution bag, one end of the liquid outlet pipeline is in communication with the liquid storage cavity, and another end of the liquid outlet pipeline is in communication with one end of the cavity inlet pipeline, another end of the cavity inlet pipeline is configured to be in communication with a body cavity, one end of the cavity outlet pipeline is configured to be in communication with the body cavity, and another end of the cavity outlet pipeline is in communication with one end of the liquid return pipeline, and another end of the liquid return pipeline is in communication with the liquid storage cavity.

18. The device of intracavitary circulatory hyperthermic perfusion of claim 17, wherein the heating tank comprises a tank body and a cover body, the tank body is hollow, and one end of the tank body is opened to form an open end, the cover body is disposed on the open end of the tank body, the cover body and the tank body together form a liquid storage cavity;
wherein the tank body comprises a tank shell and a base, the base is disposed on a bottom of the tank shell, the tank shell is made of plastic materials, and the base is made of metal materials, and the base and the tank shell are integrally formed by an injection molding; or
the tank body is integrally made of metal materials; or
the tank body has a bottom away from the open end, and the bottom of the tank body is made of metal materials.

19. The device of intracavitary circulatory hyperthermic perfusion of claim 18, wherein the heating tank further comprises an air filter and a sealing cap, a matching joint is formed on the cover body, the air filter is in communication with the liquid storage cavity through the matching joint, and the sealing cap is capable of sealing the air filter.

20. The device of intracavitary circulatory hyperthermic perfusion of claim 18, wherein the heating tank further comprises a first temperature measuring assembly comprising a first temperature sensor and a first hollow pipe, the first temperature sensor has a first probe end extending into the first hollow pipe and located on an end of the first hollow pipe, and one end of the first hollow pipe extends into the liquid storage cavity and is disposed proximate to the bottom of the tank body.

\* \* \* \* \*